US011020731B2

(12) United States Patent
Goldman et al.

(10) Patent No.: US 11,020,731 B2
(45) Date of Patent: Jun. 1, 2021

(54) CATALYSTS FOR SELECTIVE COUPLING OF OLEFINS, AND METHODS OF MAKING AND USING SAME

(71) Applicant: RUTGERS, THE STATE UNIVERSITY OF NEW JERSEY, New Brunswick, NJ (US)

(72) Inventors: Alan S. Goldman, Piscataway, NJ (US); Yang Gao, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/175,339

(22) Filed: Oct. 30, 2018

(65) Prior Publication Data

US 2019/0126260 A1 May 2, 2019

Related U.S. Application Data

(60) Provisional application No. 62/579,644, filed on Oct. 31, 2017.

(51) Int. Cl.
*B01J 31/22* (2006.01)
*C07C 2/86* (2006.01)
*B01J 31/18* (2006.01)
*C07C 2/76* (2006.01)

(52) U.S. Cl.
CPC ......... *B01J 31/2295* (2013.01); *B01J 31/182* (2013.01); *C07C 2/76* (2013.01); *C07C 2/86* (2013.01); *B01J 2231/4205* (2013.01); *B01J 2231/46* (2013.01); *B01J 2531/0244* (2013.01); *B01J 2531/827* (2013.01); *B01J 2540/10* (2013.01); *C07C 2531/22* (2013.01)

(58) Field of Classification Search
None
See application file for complete search history.

(56) References Cited

U.S. PATENT DOCUMENTS

2013/0245277 A1* 9/2013 Goldman ............... C07C 5/333
548/108

OTHER PUBLICATIONS

Gao, et al., Iridium-catalyzed dehydrogenative coupling of ethylene to form 1,3-butadiene, Rutgers University 2017 Central Regional Meeting (CERM) presentation. Jun. 8, 2017.
Gao, et al.,"β-Hydride Elimination and C—H Activation by an Iridium Acetate Complex, Catalyzed by Lewis Acids. Alkane Dehydrogenation Cocatalyzed by Lewis Acids and [2,6-Bis(4,4-dimethyloxazolinyl)-3,5-dimethylphenyl]iridium", J. Am. Chem. Soc. 2017, 139, 6338-6350.
Ito, et al., Efficient Preparation of New Rhodium- and Iridium-[Bis(oxazo-linyl)-3,5-dimethylphenyl] Complexes by C—H Bond Activation: Applications in Asymmetric Synthesis, Adv. Synth. Catal. 2006, 348, 1235-1240.
Nobbs, et al.,"Thio-Pybox and Thio-Phebox complexes of chromium, iron, cobalt and nickel and their application in ethylene and butadiene polymerisation catalysis.", Dalton Trans., 2012, 41, 5949-5964.

(Continued)

*Primary Examiner* — Yun Qian
(74) *Attorney, Agent, or Firm* — Saul Ewing Arnstein & Lehr LLP; Domingos J. Silva; Kevin T. O'Brien

(57) ABSTRACT

The present invention relates in part to the unexpected discovery of novel complexes capable of catalyzing the selective dehydrogenative coupling of olefins. The invention further relates to the use of these complexes for the selective coupling of olefins.

14 Claims, 10 Drawing Sheets

(56) References Cited

OTHER PUBLICATIONS

Zhou, et al.,"Computational Study of Pincer Iridium Catalytic Systems: C—H, N—H, and C—C Bond Activation and C—C Coupling Reactions.", A dissertation submitted to the Graduate School—New Brunswick Rutgers, The State University of New Jersey, May 2017.

* cited by examiner

CATALYSTS FOR SELECTIVE COUPLING OF OLEFINS, AND METHODS OF MAKING AND USING SAME

CROSS-REFERENCE TO RELATED APPLICATIONS

The present application claims priority under 35 U.S.C. § 119(e) to U.S. Provisional Patent Application No. 62/579,644, filed Oct. 31, 2017, which application is hereby incorporated by reference in its entirety.

STATEMENT REGARDING FEDERALLY SPONSORED RESEARCH OR DEVELOPMENT

This invention was made with government support under CHE-1205189 awarded by National Science Foundation (NSF). The government has certain rights in the invention.

BACKGROUND OF THE INVENTION 1,3-Butadiene is a "platform chemical," with about 10 M tons per annum produced for the manufacture of rubbers, polymers and chemicals. Until recently, demand for 1,3-butadiene was largely met through its production as a side-product from the cracking of naphtha, driven primarily by demand for ethylene. The recent abundance of ethane-rich shale gas, however, has shifted the production of ethylene toward the cracking of ethane. This has led to tightening supplies of 1,3-butadiene, while demand continues to increase with growth of the global economy. As a result, there is renewed interest in the development of methods for the production of 1,3-butadiene from inexpensive feedstock. The same abundance of ethane that has led to decreased butadiene production from naphtha makes ethylene an attractive potential feedstock for production of butadiene.

There is thus a need in the art for novel catalysts that can efficiently and selectively convert ethylene to 1,3-butadiene. In certain embodiments, such novel catalysts can also be used to carry out coupling of additional olefin species to generate conjugated 1,3-dienes. The present invention addresses and meets these needs.

BRIEF SUMMARY OF THE INVENTION

In one aspect, the invention provides a compound of formula (I), or a salt or solvate thereof:

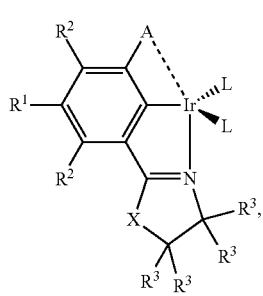

wherein:
A is selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, benzyl,

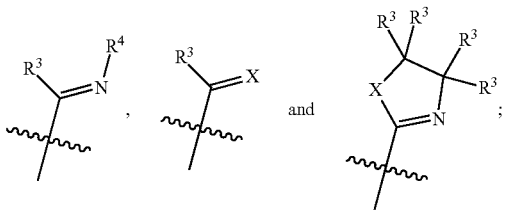

wherein at least one atom or bond in A is optionally coordinated to the Ir;

$R^1$ is selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, and benzyl;

each instance of $R^2$ is independently selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, and benzyl;

each instance of $R^3$ is independently selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, and benzyl;

each instance of $R^4$ is independently selected from the group consisting of H, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, aryl, heteroaryl, and benzyl;

X is selected from the group consisting of $CH_2$, NH, O, and S;

each occurrence of L is independently selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbene, $C_{1-6}$ alcohol, pyrrole, pyrimidine, pyrrolidine, imidazole, and

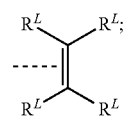

and
each instance of $R^L$ is independently selected from the group consisting of H, $C_{1-6}$ alkyl, $C_3$-$C_8$ cycloalkyl, $C_2$-$C_8$ alkenyl, $C_2$-$C_8$ alkynyl, $C_1$-$C_8$ heteroalkyl, $C_3$-$C_8$ heterocycloalkyl, $C_2$-$C_8$ heteroalkenyl, $C_{1-6}$ perhaloalkyl, aryl, heteroaryl, and benzyl.

In certain embodiments, the compound of formula (I) is a compound of formula (Ia):

(Ia)

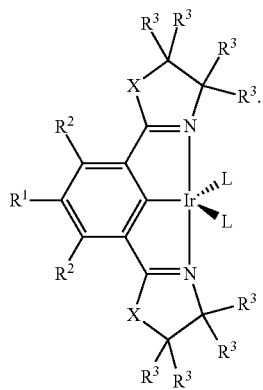

In certain embodiments, the compound of formula (I) is a compound of formula:

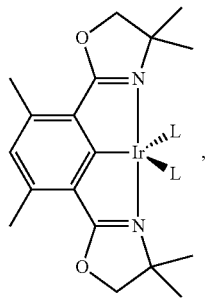

wherein L is

In certain embodiments, one instance of L is absent and the other instance of L is selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbene, $C_{1-6}$ alcohol, pyrrole, pyrimidine, pyrrolidine, imidazole, and

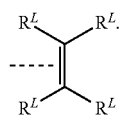

In other embodiments, L is ethylene.

In another aspect, the invention provides a compound of formula (II), or a salt or solvate thereof:

(II)

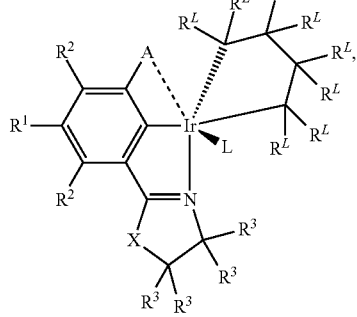

wherein:

A is selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, benzyl,

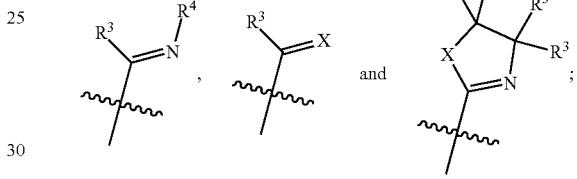

wherein at least one atom or bond in A is optionally coordinated to the Ir;

$R^1$ is selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, and benzyl;

each instance of $R^2$ is independently selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, and benzyl;

each instance of $R^3$ is independently selected from the group consisting of H, OH, halide, amine, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, $C_{1-6}$ alkoxy, aryl, heteroaryl, and benzyl;

each instance of $R^4$ is independently selected from the group consisting of H, $C_{1-6}$ alkyl, $C_3$-$C_8$ cycloalkyl, $C_1$-$C_8$ heteroalkyl, $C_3$-$C_8$ heterocycloalkyl, $C_{1-6}$ perhaloalkyl, aryl, heteroaryl, and benzyl;

X is selected from the group consisting of $CH_2$, NH, O, and S;

each occurrence of L is independently selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbene, $C_{1-6}$ alcohol, pyrrole, pyrimidine, pyrrolidine, imidazole, and

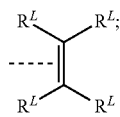

and
each instance of $R^L$ is independently selected from the group consisting of H, $C_{1-6}$ alkyl, $C_3$-$C_8$ cycloalkyl, $C_2$-$C_8$ alkenyl, $C_2$-$C_8$ alkynyl, $C_1$-$C_8$ heteroalkyl, $C_3$-$C_8$ heterocycloalkyl, $C_2$-$C_8$ heteroalkenyl, $C_{1-6}$ perhaloalkyl, aryl, heteroaryl, and benzyl.

In certain embodiments, the compound of formula (II) is:

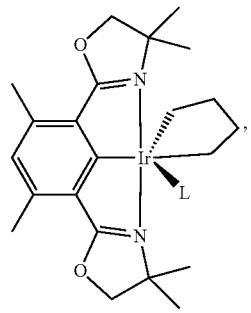

wherein L is

.

In yet another aspect, the invention provides a method of catalytically converting an olefin comprising at least one vinylic hydrogen to a conjugated 1,3-diene, the method comprising contacting the olefin with a compound of formula (I), or a salt or solvate thereof.

In certain embodiments, the compound of formula (I) is a compound of formula (IV). In other embodiments, the method comprises first contacting a compound of formula (III) with a strong base (B) to generate a compound of formula (IV), and then contacting the compound of formula (IV) with the olefin, wherein:

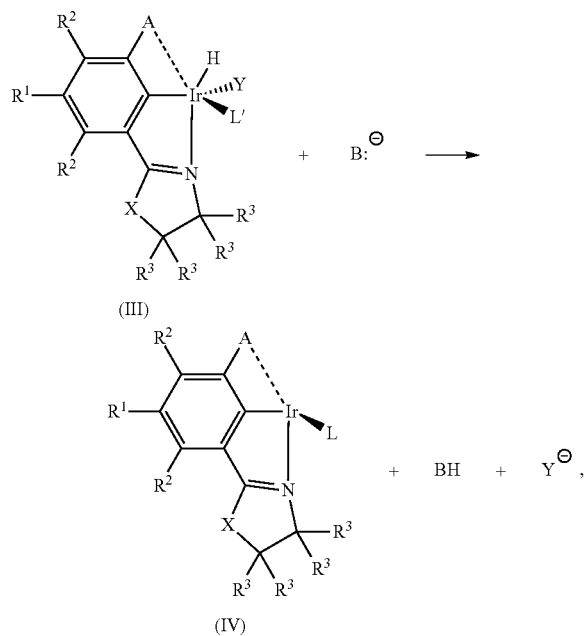

wherein either:

i) Y is selected from the group consisting of $C_{1-6}$ carboxylate, $C_{1-6}$ amide, $OR^L$, halide, amide, thiolate, oxoanion, $C_{1-6}$ alkyl, $C_{1-6}$ alkyl, $C_3$-$C_8$ cycloalkyl, $C_2$-$C_8$ alkenyl, $C_2$-$C_8$ alkynyl, $C_1$-$C_8$ heteroalkyl, $C_3$-$C_8$ heterocycloalkyl, $C_2$-$C_8$ heteroalkenyl, $C_{1-6}$ perhaloalkyl, aryl, heteroaryl, and benzyl; and L' is selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbenes, $C_{1-6}$ alcohols, pyrrole, pyrimidine, pyrrolidine, imidazole, and

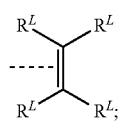

or
ii) Y and L' are a single bidentate ligand selected from the group consisting of $C_{1-6}$ carboxylate and $C_{1-6}$ amide.

In certain embodiments, the olefin pressure ranges from about 0.1 atm to about 100 atm. In other embodiments, the catalyst is contacted with the alkene at a temperature of about 100° C. to about 200° C.

In certain embodiments, the olefin comprises ethylene. In other embodiments, the conjugated 1,3-diene comprises 1,3-butadiene.

In certain embodiments, the catalyst is in solution. In other embodiments, the solution comprises at least one solvent selected from the group consisting of toluene, benzene, xylenes, dioxane, heptane, pyridine, tetrahydrofuran, acetone, acetonitrile, butanol, butanone, carbon tetrachloride, chlorobenzene, chloroform, cyclohexane, dichloroethane, diethylene glycol, diethyl ether, diglyme, dimethyl formamide, dimethyl sulfoxide, ethanol, ethyl acetate, ethylene glycol, glycerin, hexamethylphosphoramide, hexamethylphosphorous triamide, hexanes, methanol, methylene chloride, N-methyl-2-pyrrolidinone, nitromethane, pentane, petroleum ether, propanol, and triethylamine. In yet other embodiments, the solution further comprises at least one hydrogen acceptor additive.

BRIEF DESCRIPTION OF THE DRAWINGS

For the purpose of illustrating the invention, certain embodiments of the invention are depicted in the drawings. However, the invention is not limited to the precise arrangements and instrumentalities of the embodiments depicted in the drawings.

(FIG. 4B), TS for β-H-elimination TS2 (FIG. 4C), and the initial product of β-H-elimination 9 (FIG. 4D), highlighting the distortion required to allow the agostic interaction and the geometrical similarity of 8, TS2, and 9. H atom undergoing migration to Ir is marked with an *, other 1,4-butanediyl H atoms are unlabeled. Otherwise, gray unlabeled atoms are carbon atoms, and white unlabeled atoms are hydrogen atoms.

DETAILED DESCRIPTION OF THE INVENTION

Figure 1:
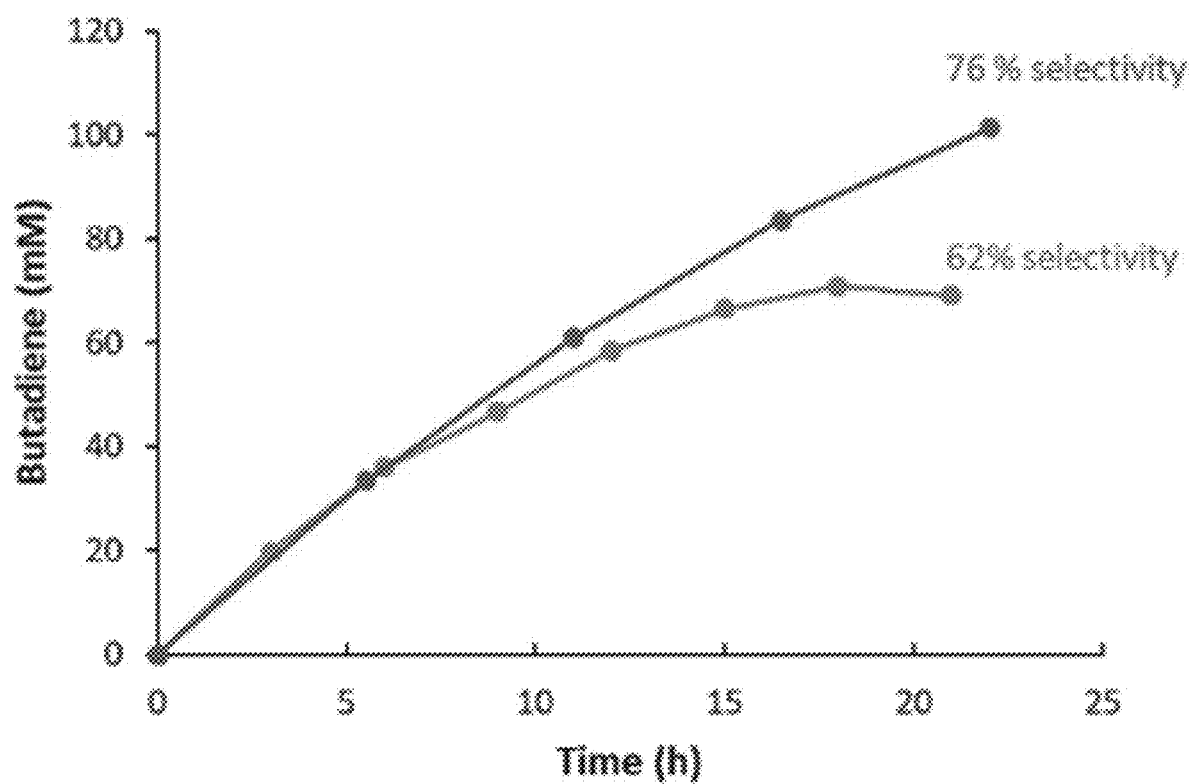
FIG. 1 is a graph tracking the production of 1,3-butadiene from ethylene, catalyzed by 2. Conditions: 5.0 mM 2 in toluene-$d_8$ $C_2H_4$ (12 atm), 110° C., volatiles removed every 5.5 h (upper curve) followed by recharging with toluene-$d_8$ and $C_2H_4$, or allowed to remain in solution (lower curve).

The present invention relates in part to the unexpected discovery of novel complexes capable of catalyzing selective dehydrogenative coupling of olefins. The invention further relates to the use of these complexes for selective dehydrogenative coupling of olefins.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in separation science, organometallic chemistry, inorganic chemistry, and organic chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "alkenyl," employed alone or in combination with other terms, means, unless otherwise stated, a stable monounsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH$_2$—CH=CH$_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. A specific example is (C$_1$-C$_3$)alkoxy, such as, but not limited to, ethoxy and methoxy.

As used herein, the term "alkyl," by itself or as part of another substituent means, unless otherwise stated, a straight or branched chain hydrocarbon having the number of carbon atoms designated (i.e., C$_1$-C$_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A selected example is (C$_1$-C$_6$)alkyl, such as, but not limited to, ethyl, methyl, isopropyl, isobutyl, n-pentyl, n-hexyl and cyclopropylmethyl.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH. The term "substituted propargylic" refers to a group exemplified by —CR$_2$—C≡CR', wherein each occurrence of R' is independently H, alkyl, substituted alkyl, alkenyl or substituted alkenyl, with the proviso that at least one R' group is not hydrogen. The term "substituted homopropargylic" refers to a group exemplified by —CR'$_2$CR'$_2$—C≡CR', wherein each occurrence of R' is independently H, alkyl, substituted alkyl, alkenyl or substituted alkenyl, with the proviso that at least one R' group is not hydrogen.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl.

As used herein, the term "aryl-(C$_1$-C$_3$)alkyl" refers to a functional group wherein a one to three carbon alkylene chain is attached to an aryl group, e.g., —CH$_2$CH$_2$-phenyl or —CH$_2$-phenyl (benzyl). Specific examples are aryl-CH$_2$— and aryl-CH(CH$_3$)—. The term "substituted aryl-(C$_1$-C$_3$) alkyl" refers to an aryl-(C$_1$-C$_3$)alkyl functional group in which the aryl group is substituted. A specific example is substituted aryl(CH$_2$)—. Similarly, the term "heteroaryl-(C$_1$-C$_3$)alkyl" refers to a functional group wherein a one to three carbon alkylene chain is attached to a heteroaryl group, e.g., —CH$_2$CH$_2$-pyridyl. A specific example is heteroaryl-(CH$_2$)—. The term "substituted heteroaryl-(C$_1$-C$_3$)alkyl" refers to a heteroaryl-(C$_1$-C$_3$)alkyl functional group in which the heteroaryl group is substituted. A specific example is substituted heteroaryl-(CH$_2$)—.

As used herein, the term "conjugated 1,3-diene" refers to a molecule that comprises the group

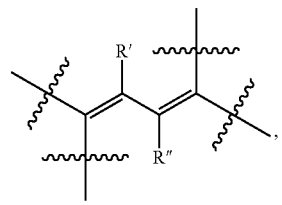

wherein R' and R" are independently H or a non-H-substituent. In certain embodiments, the conjugated 1,3-diene is 1,3-butadiene.

As used herein, the term "cracking" refers to the petrochemistry process whereby complex organic molecules are broken down into lower-molecular weight molecules through the breaking of carbon-carbon bonds and/or loss of hydrogen gas.

As used herein, the term "cycloalkyl," by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Other examples are ($C_3$-$C_6$)cycloalkyl, such as, but not limited to, cyclopropyl, cyclobutyl, cyclopentyl and cyclohexyl.

As used herein,

refers to a side-on bound ethylene. The dashed bond to the center of the ethylene denotes an $\eta^2$ coordination to a metal center. Analogously,

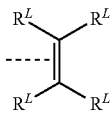

refers to a side-on bound ethylene substituted with $R^L$. The substitutions on the ethylene are as defined elsewhere herein, constituting a genus of $\eta^2$ coordinated olefin ligands.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclic and heteroaryl moieties is intended to be representative and not limiting.

As used herein, the term "ligand" refers to any organic or inorganic molecule or ion that is capable of coordinating to a metal center. In certain embodiments, the ligand comprises one or more lone electrons or electron pairs that can coordinate with a metal center.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined above, substituted by one, two or three substituents selected from the group consisting of halogen, —OH, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(=O)OH, trifluoromethyl, —C(=O)O(C$_1$-C$_4$)alkyl, —C(=O)NH$_2$, —C(=O)NH(C$_1$-C$_4$)alkyl, —C(=O)N((C$_1$-C$_4$)alkyl)$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In another embodiment, the substituents vary in number between one and three. In yet another embodiment, the substituents vary in number between one and two. In yet another embodiment, the substituents are independently selected from the group consisting of C$_{1-6}$ alkyl, —OH, C$_{1-6}$ alkoxy, halo, amino, acetamido and nitro. As used herein, where a substituent is an alkyl or alkoxy group, the carbon chain may be branched, straight or cyclic.

In certain embodiments, an optional substituent is selected from the group consisting of C$_1$-C$_6$ alkyl, C$_3$-C$_8$ cycloalkyl, phenyl, C$_1$-C$_6$ hydroxyalkyl, (C$_1$-C$_6$ alkoxy)-C$_1$-C$_6$ alkyl, C$_1$-C$_6$ haloalkyl, C$_1$-C$_6$ haloalkoxy, halogen, —CN, —OR$^b$, —N(R$^b$)(R$^b$), —NO$_2$, —C(=O)N(R$^b$)(R$^b$), —S(=O)$_2$N(R$^b$)(R$^b$), acyl, and C$_1$-C$_6$ alkoxycarbonyl, wherein each occurrence of R$^b$ is independently H, C$_1$-C$_6$ alkyl, or C$_3$-C$_8$ cycloalkyl, wherein in R$^b$ the alkyl or cycloalkyl is optionally substituted with at least one selected from the group consisting of halogen, —OH, C$_1$-C$_6$ alkoxy, and heteroaryl; or substituents on two adjacent carbon atoms combine to form —O(CH$_2$)$_{1-3}$O—.

In certain embodiments, an optional substituent is selected from the group consisting of C$_1$-C$_6$ alkyl, C$_3$-C$_8$ cycloalkyl, phenyl, C$_1$-C$_6$ hydroxyalkyl, (C$_1$-C$_6$ alkoxy)-C$_1$-C$_6$ alkyl, C$_1$-C$_6$ haloalkyl, C$_1$-C$_6$ haloalkoxy, halogen, —OR$^b$, and —C(=O)N(R$^b$)(R$^b$), wherein each occurrence of R$^b$ is independently H, C$_1$-C$_6$ alkyl, or C$_3$-C$_8$ cycloalkyl, wherein in R$^b$ the alkyl or cycloalkyl is optionally substituted with at least one selected from the group consisting of halogen, —OH, C$_1$-C$_6$ alkoxy, and heteroaryl; or substituents on two adjacent carbon atoms combine to form —O(CH$_2$)$_{1-3}$O—.

In certain embodiments, an optional substituent is selected from the group consisting of C$_1$-C$_6$ alkyl, —OH, C$_1$-C$_3$ haloalkyl, C$_1$-C$_6$ alkoxy, C$_3$-C$_8$ cycloalkyl, C$_3$-C$_8$ cycloalkoxy, halo, and —CN.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Disclosure

The present invention relates to the unexpected discovery of novel transition metal catalysts that are useful in the dehydrogenative coupling of olefins. In certain embodiments, the catalysts are capable of carrying out the selective and efficient conversion of ethylene to 1,3-butadiene.

In one aspect, the invention provides a compound of formula (I), or a salt or solvate thereof:

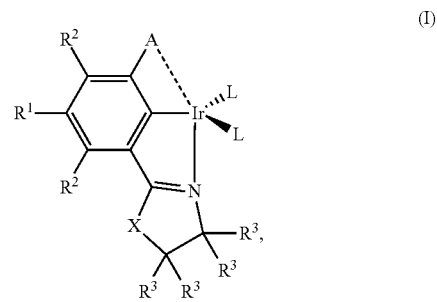

(I)

wherein;

A is selected from the group consisting of H, OH, halide, amine, optionally substituted C$_{1-6}$ alkyl, optionally substituted C$_3$-C$_8$ cycloalkyl, optionally substituted C$_1$-C$_8$ heteroalkyl, optionally substituted C$_3$-C$_8$ heterocycloalkyl, optionally substituted C$_{1-6}$ perhaloalkyl, optionally substituted C$_{1-6}$ alkoxy, optionally substituted aryl, optionally substituted heteroaryl, optionally substituted benzyl,

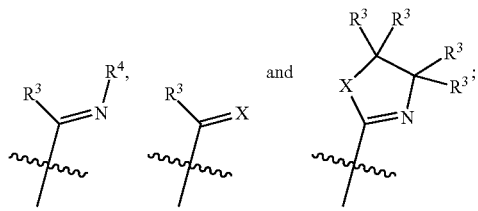

wherein at least one atom or bond in A is optionally coordinated to the Ir;

R$^1$ is selected from the group consisting of H, OH, halide, amine, optionally substituted C$_{1-6}$ alkyl, optionally substituted C$_3$-C$_8$ cycloalkyl, optionally substituted C$_1$-C$_8$ heteroalkyl, optionally substituted C$_3$-C$_8$ heterocycloalkyl, optionally substituted C$_{1-6}$ perhaloalkyl, optionally substituted C$_{1-6}$ alkoxy, optionally substituted aryl, optionally substituted heteroaryl, and optionally substituted benzyl;

each instance of R$^2$ is independently selected from the group consisting of H, OH, halide, amine, optionally substituted C$_{1-6}$ alkyl, optionally substituted C$_3$-C$_8$ cycloalkyl, optionally substituted C$_1$-C$_8$heteroalkyl, optionally substituted C$_3$-C$_8$ heterocycloalkyl, optionally substituted C$_{1-6}$ perhaloalkyl, optionally substituted C$_{1-6}$ alkoxy, optionally substituted aryl, optionally substituted heteroaryl, and optionally substituted benzyl;

each instance of R$^3$ is independently selected from the group consisting of H, OH, halide, amine, optionally substituted C$_{1-6}$ alkyl, optionally substituted C$_3$-C$_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, and optionally substituted benzyl;

each instance of $R^4$ is independently selected from the group consisting of H, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted aryl, optionally substituted heteroaryl, and optionally substituted benzyl;

X is selected from the group consisting of $CH_2$, NH, O, and S;

each occurrence of L is independently selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbene, $C_{1-6}$ alcohol, pyrrole, pyrimidine, pyrrolidine, imidazole, and

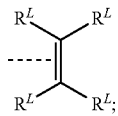

and each instance of $R^L$ is independently selected from the group consisting of H, optionally substituted $C_{1-6}$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted $C_{1-6}$ perhaloalkyl, optionally substituted aryl, optionally substituted heteroaryl, and optionally substituted benzyl.

In certain embodiments, the compound of formula (I) is a compound of formula (Ia):

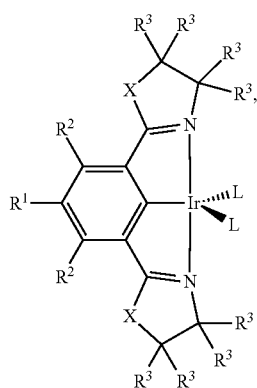

wherein $R^1$, $R^2$, $R^3$, $R^L$, X and L are as defined in formula (I).

In certain embodiments, the compound of formula (I) is:

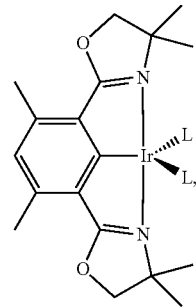

wherein L is

(ethylene).

In certain embodiments, one instance of L is absent while the other instance of L is not.

In certain embodiments, the compound of formula (I) comprises an Ir (I).

In another aspect, the invention provides a compound of formula (II), or a salt or solvate thereof:

(II)

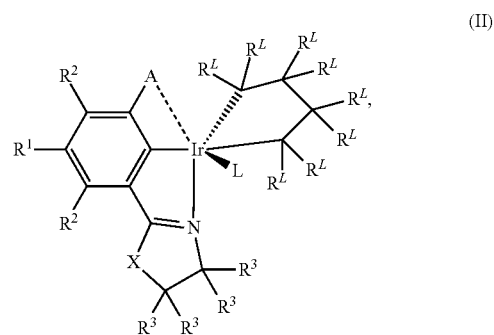

wherein;

A is selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, optionally substituted benzyl,

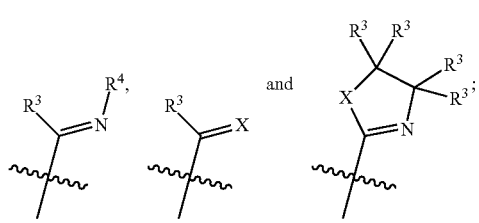

wherein at least one atom or bond in A is optionally coordinated to the Ir;

$R^1$ is selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, and optionally substituted benzyl;

each instance of $R^2$ is independently selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, and optionally substituted benzyl;

each instance of $R^3$ is independently selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, and optionally substituted benzyl;

each instance of $R^4$ is independently selected from the group consisting of H, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted aryl, optionally substituted heteroaryl, and optionally substituted benzyl;

X is selected from the group consisting of $CH_2$, NH, O and S;

each occurrence of L is independently selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbene, $C_{1-6}$ alcohol, pyrrole, pyrimidine, pyrrolidine, imidazole, and

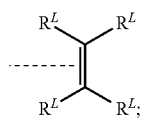

and each instance of $R^L$ is independently selected from the group consisting of H, optionally substituted $C_{1-6}$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted $C_{1-6}$ perhaloalkyl, optionally substituted aryl, optionally substituted heteroaryl, and optionally substituted benzyl.

In certain embodiments, the compound of formula (II) is:

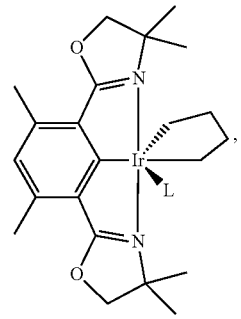

wherein L is

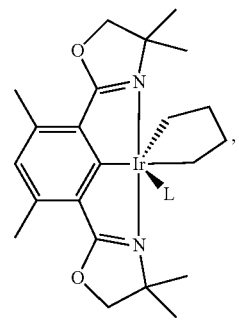

(ethylene).

In certain embodiments, the compound of formula (II) comprises an Ir (I).

In another aspect, the invention provides compounds, which are precatalysts and, upon activation, can be used for the catalytic homocoupling of olefins. In certain embodiments, a precatalyst of the invention is a compound of formula (III), or a salt or solvate thereof:

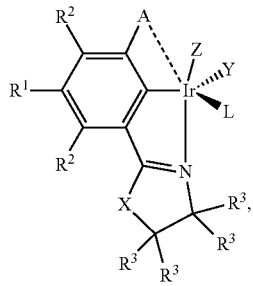

(III)

wherein;

A is selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, optionally substituted benzyl,

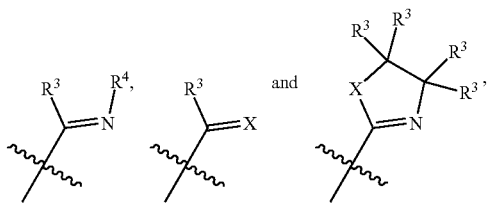

wherein at least one atom or bond in A is optionally coordinated to the Ir;

R¹ is selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, and optionally substituted benzyl;

each instance of R² is independently selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, and optionally substituted benzyl;

each instance of R³ is independently selected from the group consisting of H, OH, halide, amine, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted $C_{1-6}$ alkoxy, optionally substituted aryl, optionally substituted heteroaryl, and optionally substituted benzyl;

each instance of R⁴ is independently selected from the group consisting of H, optionally substituted $C_{1-6}$ alkyl, optionally substituted $C_3$-$C_8$ cycloalkyl, optionally substituted $C_1$-$C_8$ heteroalkyl, optionally substituted $C_3$-$C_8$ heterocycloalkyl, optionally substituted $C_{1-6}$ perhaloalkyl, optionally substituted aryl, optionally substituted heteroaryl, and optionally substituted benzyl;

X is selected from the group consisting of $CH_2$, NH, O, and S;

Z is selected from the group consisting of H, $C_{1-6}$ carboxylate, $OR^L$, halide, amide, thiolate, oxoanion, $C_{1-6}$ alkyl, optionally substituted $C_{1-6}$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted $C_{1-6}$ perhaloalkyl, optionally substituted aryl, optionally substituted heteroaryl, and optionally substituted benzyl;

either:

i) Y is selected from the group consisting of $C_{1-6}$ carboxylate, $C_{1-6}$ amide, $OR^L$, halide, amide, thiolate, oxoanion, $C_{1-6}$ alkyl, optionally substituted $C_{1-6}$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted $C_{1-6}$ perhaloalkyl, optionally substituted aryl, optionally substituted heteroaryl, and optionally substituted benzyl; and L is selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbenes, $C_{1-6}$ alcohols, pyrrole, pyrimidine, pyrrolidine, imidazole, and

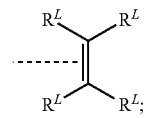

or ii) Y and L are a single bidentate ligand selected from the group consisting of $C_{1-6}$ carboxylate and $C_{1-6}$ amide; and each instance of $R^L$ is independently selected from the group consisting of H, optionally substituted $C_{1-6}$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted $C_{1-6}$ perhaloalkyl, optionally substituted aryl, optionally substituted heteroaryl, and optionally substituted benzyl.

In certain embodiments, Y is not acetate. In other embodiments, wherein Y and L are a single bidentate ligand, Y and L are not acetate.

In certain embodiments, Z is H.

In certain embodiments, the compound of formula (III) is a compound of formula (IIIa):

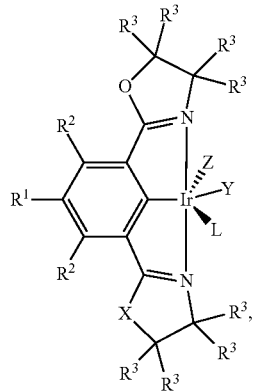

(IIIa)

wherein R¹, R², R³, $R^L$, X, Y, Z and L are as defined in formula (III).

In other embodiments, the compound of formula (III) is:

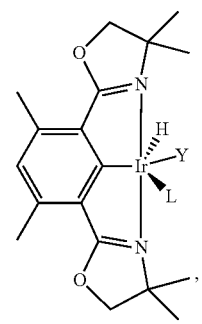

wherein Y is as defined in formula (III) and L is

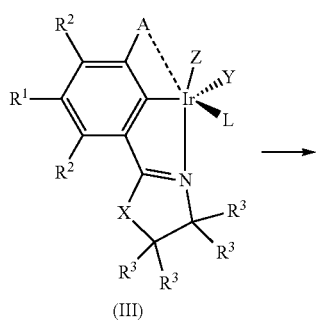

In certain embodiments, the compound of formula (III) comprises an Ir (III).

In certain embodiments, the compound of formula (III) can form a compound of formula (IV) through reductive elimination of Z—Y:

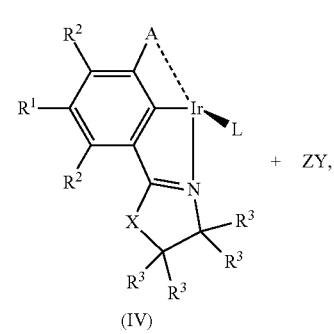

wherein $R^1$, $R^2$, $R^3$, $R^L$, X, Y, Z and L are defined as in formula (III).

In certain embodiments wherein Z is H, the compound of formula (III) can be contacted with a strong base to form a compound of formula (IV):

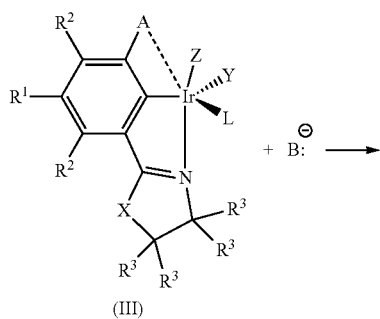

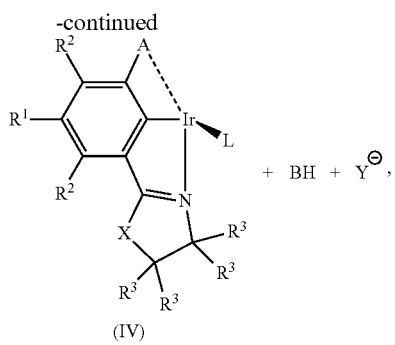

wherein $R^1$, $R^2$, $R^3$, $R^{1-}$, X, Y and L are defined as in formula (III).

In certain embodiments, the compound of formula (IV) comprises an Ir (I).

Methods

The compounds of formula (I), formula (II) or formula (III) can be used in coupling reactions to promote the catalytic formation of C—C bonds between olefins. In certain embodiments, the compounds of formula (I), formula (II) or formula (III) can be used to promote the reaction depicted in Scheme 1:

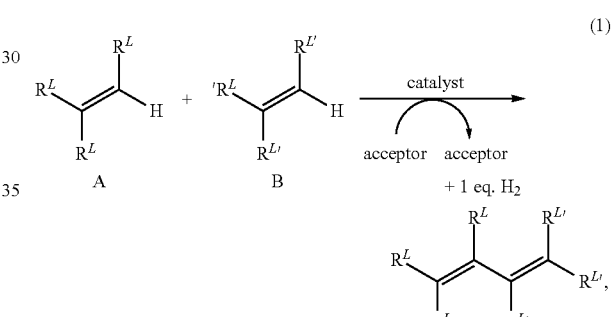

wherein each instance of $R^L$ and is independently selected from the group consisting of H, optionally substituted $C_{1-6}$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted $C_{1-6}$ perhaloalkyl, optionally substituted aryl, optionally substituted heteroaryl, and optionally substituted benzyl.

In certain embodiments, the olefins comprise at least one vinylic hydrogen.

In certain embodiments, the invention includes a method of catalytically coupling two or more olefins to form a single di-unsaturated molecule. In certain embodiments, the two or more olefins are identical. In other embodiments, at least one olefin is distinct from at least one other olefin.

In certain embodiments, the method comprises contacting a compound of formula (I) with an olefin. In other embodiments, the method comprises contacting a compound of formula (II) with an olefin. In yet other embodiments, the method comprises first contacting a compound of formula (III), wherein Z is H, with a strong base, whereby the hydride and Y ligand are removed from the metal center to form a catalytically active compound of formula (IV), which is then contacted with an olefin.

In certain embodiments, the compound of formula (I), (II), or (IV) is contacted with the olefin under high pressure. In other embodiments, the olefin pressure ranges from about 2 atm to about 12 atm, but it not necessarily limited to this range.

In certain embodiments, the compound of formula (I), (II), or (IV) is contacted with the olefin at a temperature of about 100° C. to about 200° C. In other embodiments, the olefin is contacted at a temperature of about 100° C. to about 110° C.

In certain embodiments, the compound of formula (I), (II), or (IV) is contacted with the olefin in solution. In other embodiments, the solution is a non-aqueous solution. In yet other embodiments, the solution comprises a solvent selected from, but not necessarily limited to, the group consisting of toluene, benzene, xylenes, dioxane, heptane, pyridine, tetrahydrofuran, acetone, acetonitrile, butanol, butanone, carbon tetrachloride, chlorobenzene, chloroform, cyclohexane, dichloroethane, diethylene glycol, diethyl ether, diglyme, dimethyl formamide, dimethyl sulfoxide, ethanol, ethyl acetate, ethylene glycol, glycerin, hexamethylphosphoramide, hexamethylphosphorous triamide, hexanes, methanol, methylene chloride, N-methyl-2-pyrrolidinone, nitromethane, pentane, petroleum ether, propanol and trimethylamine.

In certain embodiments, the solution further comprises at least one acceptor capable of accepting an equivalent of $H_2$. In other embodiments, the acceptor is a hydrogen acceptor. In yet other embodiments, the acceptor is an olefin. In yet other embodiments, the acceptor is an additional equivalent of olefin A or B from Scheme 1.

In certain embodiments, the olefins are ethylene. In other embodiments, the conjugated 1,3-diene product is 1,3-butadiene.

In certain embodiments, the method comprises contacting a compound of formula

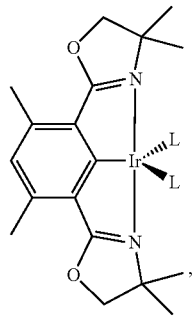

wherein L is

with ethylene.

In certain embodiments, the method further comprises removing the di-unsaturated product from the reaction mixture as it is produced. In other embodiments, the di-unsaturated product is removed from the reaction mixture in vacuo. In yet other embodiments, the di-unsaturated product is removed from the reaction mixture through distillation. In certain embodiments, by removing the di-unsaturated product from the reaction mixture as it is produced, the overall reaction yield and selectivity is increased.

The invention further provides methods, as well as systems which utilize the compounds and methods of the invention, for converting an organic feedstock to a conjugated 1,3-diene.

In certain embodiments, the method comprises subjecting an organic feedstock to a cracking process in order to produce ethylene, and then contacting the ethylene product with a compound of formula (I), formula (II) or formula (IV) in order to produce 1,3-butadiene. In other embodiments, the organic feedstock is selected from the group consisting of shale gas, methane and ethane.

Figure 6:
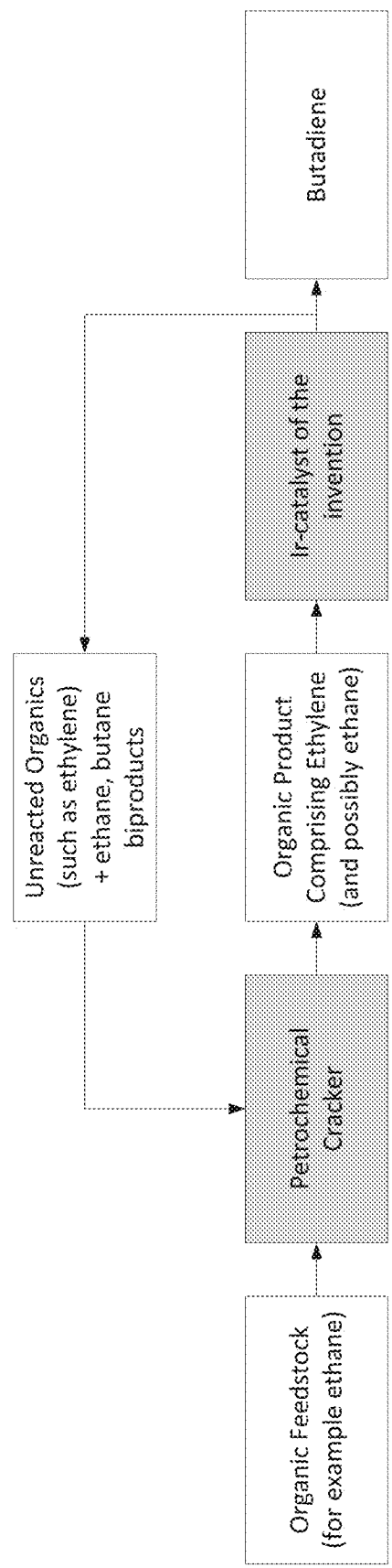
FIG. 6 is a schematic of a system of the invention describing how the methods of the invention can be coupled to petrochemical cracking processes in order to convert raw organic chemical feedstocks into a conjugated 1,3-diene.

In certain embodiments, the cracking process does not completely convert all of the organic starting materials into ethylene. In other embodiments, the mixed cracking products can be contacted with compound of formula (I), formula (II) or formula (IV) and then any non-butadiene organics (unreacted organics as well as any potential organic byproducts such as ethane, butane and butene) can be recycled and re-subjected to the cracking process (FIG. 6).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so on, as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

Unless specified otherwise, all reactions were conducted under an argon atmosphere using an MBraun glovebox, or Schlenk or vacuum-line techniques. Anhydrous benzene and p-xylene were purchased from Sigma-Aldrich, stored over molecular sieves in the glovebox and used without further purification. Benzene-$d_6$, toluene-$d_8$ and p-xylene-$d_{10}$ were purchased from Cambridge Isotope Labs, dried over activated alumina and filtered. All other reagents were purchased from commercial suppliers and used without further purification. Medium-walled NMR tubes (maximum pressure: 150 psi) and heavy-walled Wilmad quick pressure valve NMR tubes (maximum pressure: 200 psi) were purchased from Sigma-Aldrich. NMR spectra were acquired on 500 MHz Varian VNMRS NMR spectrometers and $^1$H and $^{13}$C spectra are referenced to residual solvent peaks. The signal of the residual protio methyl group of p-xylene-$d_{10}$ was set at δ 20.90 in the $^{13}$C NMR spectrum.

Synthesis and Characterization of Complexes (Phebox)Ir(OAc)$_2$(OH$_2$)

(Phebox)Ir(OAc)$_2$(OH$_2$) was prepared according to published procedures (Ito, J.-i.; Shiomi, T.; Nishiyama, H. *Adv. Synth. Catal.* 2006, 348, 1235-1240). Briefly, a mixture of Phebox-H, IrCl$_3$(H$_2$O)$_3$, and NaHCO$_3$ was heated in methanol to give (Phebox)Ir(Cl)$_2$(H$_2$O). This was converted to the acetate complex (Phebox)Ir(OAc)$_2$(OH$_2$) by treatment with an excess of silver acetate in high yield.

(Phebox)Ir(OAc)(H) (1)

(Phebox)Ir(OAc)$_2$(OH$_2$) (50 mg, 0.0080 mmol) and 5 mL 2-propanol were added to a 50-mL Teflon-stoppered reaction vessel under argon atmosphere and then heated at 100° C. for 2 h. Volatiles were then removed in vacuo. Complex 2 was obtained in 98% yield (by NMR). Further purification was achieved by recrystallization from diethyl ether/pentane at −32° C. 1H NMR (C$_6$D$_6$, 500 MHz): δ6.49 (s, 1H), 3.85 (d, J=8.3 Hz, 2H), 3.80 (d, J=8.3 Hz, 2H), 2.64 (s, 6H), 2.05 (s, 3H), 1.33 (s, 6H), 1.29 (s, 6H), −33.80 (s, 1H). 13C NMR (C$_6$D$_6$, 125 MHz): δ185.8, 178.6, 177.2, 139.4, 126.9, 123.0, 81.6, 65.7, 27.3, 26.6, 26.3, 18.9. Anal. Calcd. for 2-H: C, 43.54; H, 4.93; N, 5.08. Found: C, 43.11; H: 4.74; N, 4.70.

(Phebox)Ir(η$^2$-ethylene)$_2$ (2)

1 (11 mg, 0.020 mmol) and 2.5 mL benzene were added to a 25-mL Schlenk flask in a glovebox. The flask was removed from the glovebox and charged with 1 atm of ethylene. A benzene solution of NaOtBu (4.8 mg, 0.050 mmol) was added via syringe dropwise through the septum at room temperature. After 24 h, the volatiles were removed under vacuum and the product was redissolved in toluene (2.5 mL). The clear solution was filtered using a cannula filter. Subsequently, the residue was washed with additional toluene (2.5 mL) and then combined with initial toluene solution. Removal of the volatiles under vacuum resulted in a bright orange powder. Yield: 8.3 mg (76%). 1H NMR (C$_6$D$_6$, 500 MHz): δ6.68 (s, 1H), 3.41 (s, 4H), 3.45-3.32 (m, 4H), 2.66 (s, 6H), 1.65-1.50 (m, 4H), 0.73 (s, 12H). 13C NMR (C$_6$D$_6$, 125 MHz): δ211.1, 178.0, 138.2, 129.0, 126.6, 81.3, 67.8, 31.9, 26.4, 19.0, 10.8. Anal. Calcd. for 3: C, 48.24; H, 5.71; N, 5.11. Found: C, 47.78; H: 5.40; N, 4.86.

(Phebox)Ir(C$_4$H$_8$)(C$_2$H$_4$) (3)

2 (2.2 mg, 4.0 μmol) and 0.4 mL p-xylene (2.0 mM) in C$_6$D$_6$ solution were added to a J-Young NMR tube in the glovebox. The solution was degassed using one freeze-pump-thaw cycle, charged with 1 atm of ethylene and heated at 70° C. for 18 h. NMR yield: 71%. $^1$H NMR (C$_6$D$_6$, 500 MHz): δ 6.66 (t, J=7.1 Hz, 2H), 3.55 (d, J=8.2 Hz, 2H), 3.48 (d, J=8.2 Hz, 2H), 2.86 (br s, 4H), 2.64 (s, 6H), 2.55 (m, 2H), 2.17 (m, 2H), 1.53 (t, J=6.8 Hz, 2H), 1.13 (s, 6H), 0.82 (s, 6H). $^{13}$C NMR (C$_6$D$_6$, 125 MHz): δ 204.8, 178.0, 139.7, 127.0, 126.7, 81.6, 67.7, 53.2, 40.6, 36.4, 29.9, 27.9, 27.4, 19.1, 2.7.

(Phebox)Ir(η$^2$-ethylene-$^{13}$C$_2$)$_2$ (2-$^{13}$C$_4$)

(Phebox)Ir(OAc)(H) (4.4 mg, 8.0 μmol), NaO$^t$Bu (2.2 mg, 24 μmol) and 0.5 mL p-xylene were added to a J-Young NMR tube in the glovebox. The solution was degassed using one freeze-pump-thaw cycle and charged with 1 atm of ethylene-$^{13}$C$_2$. After heating at 40° C. for 4 h, the volatiles were removed under vacuum and the product was re-dissolved in toluene (1 mL). Bright orange powder was achieved after filtration and removal of solvent under vacuum. Yield: 3.2 mg (73%). $^1$H NMR (p-xylene-$d_{10}$, 500 MHz): 6.61 (s, 1H), 3.57 (s, 4H), 3.45-3.03 (m, $^1J^{13}{}_{C-H}$=151.6 Hz, 4H), 2.65 (s, 4H), 1.60-1.18 (m, 4H), 0.82 (s, 12H). $^{13}$C NMR of ethylene-$^{13}$C$_2$ ligand (p-xylene-$d_{10}$, 125 MHz): δ 32.8 (d, J=41.7 Hz), 11.6 (d, J=41.9 Hz).

(Phebox)Ir(C$_4$H$_8$-$^{13}$C$_4$)(C$_2$H$_4$-$^{13}$C$_2$)(3-$^{13}$C$_6$)

Following the procedure above to synthesize 3, 2-$^{13}$C$_4$ (10 mM) in p-xylene-$d_{10}$ solution (0.4 mL) was heated under ethylene-$^{13}$C$_2$ (1 atm) at 70° C. for 18 h. NMR yield: 70%. $^{13}$C NMR of $^{13}$C labelled ligand (p-xylene-$d_{10}$, 125 MHz): δ 54.1, 41.3 (ddd, J=36.7, 32.3, 4.2 Hz), 37.2 (dd, J=36.9, 31.9 Hz), 31.2-29.8 (m), 3.5 (dd, J=32.0, 4.3 Hz).

(Phebox)Ir(C$_4$H$_8$-$^{13}$C$_4$)(C$_2$H$_4$) (3-$^{13}$C$_4$)

3-$^{13}$C$_6$ (7.0 mM) and 2-$^{13}$C$_4$ (3.0 mM) in p-xylene-$d_{10}$ solution (0.4 mL) was added to a J-Young NMR tube in the glovebox. The solution was degassed using one freeze-pump-thaw cycle and charged with 1 atm of ethylene. 3-$^{13}$C$_4$ (7.0 mM) and 2 (3.0 mM) was formed at room temperature. $^{13}$C NMR of $^{13}$C labelled ligand (p-xylene-$d_{10}$, 125 MHz): δ 41.3 (ddd, J=36.6, 32.3, 4.2 Hz), 37.2 (dd, J=36.8, 32.1 Hz), 31.6-29.6 (m), 3.5 (dd, J=32.0, 4.3 Hz).

1,3-Butadiene-$^{13}$C$_4$

3-$^{13}$C$_6$ (7.0 mM) and 2-$^{13}$C$_4$ (3.0 mM) in p-xylene-$d_{10}$ solution (0.4 mL) was added to a medium-walled and sealable NMR tube, which was connected to a Kontes high-vacuum adapter with Tygon tubing. The Kontes valve was attached to a vacuum-gas manifold and the solution was frozen with liquid nitrogen. The headspace of NMR tube was evacuated until the pressure reached 10 mTorr. The headspace was filled with 1 atm of ethylene-$^{13}$C$_2$ and then condensed using liquid nitrogen. After 30 seconds, the NMR tube was sealed using an oxygen torch (the headspace volume was decreased by 50%, which brought the total ethylene pressure to 2 atm). The sealed NMR tube was allowed to reach room temperature, then heated and rotated in a GC oven at 100° C. for 1 h. $^{13}$C NMR (p-xylene-$d_{10}$, 125 MHz): δ 143.3-142.1 (m), 122.7-121.1 (m).

(Phebox)Ir(OAc)(CH$_2$(CH$_2$)$_2$CH$_3$) (4)

Following a procedure outlined in Gao, Y, et al. *J. Am. Chem. Soc.* 2017, 139, 6338, the reaction was set up under 1 atm of 1-butene and finished in 15 minutes at room temperature. Briefly, 1 (2.2 mg, 0.004 mmol), NaBArF (0.6 mg, 0.7 μmol), 400 μL of benzene and 10 μL of 0.117 M dioxane in benzene solution were added to a J-Young NMR tube in a glovebox. The solution was degassed using one freeze-pump-thaw cycle and then charged with 1 atm of 1-butene. The reaction was finished in 15 minutes at room temperature.

NMR yield: 98%. $^1$H NMR (C$_6$D$_6$, 500 MHz): δ 6.48 (s, 1H), 3.86-3.80 (m, 4H), 2.64 (s, 6H), 2.07 (s, 3H), 1.69 (m, 2H), 1.41 (m, 2H), 1.36 (s, 6H), 1.28 (s, 6H), 0.98 (m, 3H), 0.63-0.51 (m, 2H). $^{13}$C NMR (C$_6$D$_6$, 125 MHz): δ 184.3, 182.1, 177.3, 139.3, 126.0, 123.2, 82.0, 66.2, 33.7, 27.2, 27.0, 25.9, 24.6, 19.0, 14.6, −3.8.

(Phebox)Ir($C_4H_8$)(CO) (6)

3 (7.0 mM) and 2 (3.0 mM) in $C_6D_6$ solution (0.4 mL) was added to a J-Young NMR tube in the glovebox. The solution was degassed using one freeze-pump-thaw cycle and charged with 1 atm of CO. 6 (7.0 mM) and 5 (3.0 mM) was formed at room temperature. $^1$H NMR of 6 ($C_6D_6$, 500 MHz): δ 6.61 (s, 1H), 3.70-3.58 (m, 4H), 3.24 (t, J=7.1 Hz, 2H), 2.58 (s, 7H), 2.47 (m, 2H), 2.14 (m, 2H), 1.18 (s, 6H), 1.13 (s, 6H), 1.02 (t, J=6.8 Hz, 2H). $^{13}$C NMR of 6 ($C_6D_6$, 125 MHz): δ 194.7, 178.6, 175.6, 140.4, 127.4, 127.0, 81.4, 67.1, 39.3, 36.9, 32.7, 28.4, 28.3, 19.1, 1.2.

(Phebox)Ir(CO) (5)

6 (7.0 mM) and 5 (3.0 mM) in $C_6D_6$ solution (0.4 mL) was added to a J-Young NMR tube in the glovebox. After heating at 90° C. for 1 h, the volatiles were removed under vacuum and the products were re-dissolved in $C_6D_6$. 5 (8.2 mM) was obtained with free Phebox-H (1.5 mM) as the side product. $^1$H NMR ($C_6D_6$, 500 MHz): δ 6.40 (s, 1H), 3.73 (s, 4H), 2.30 (s, 6H), 1.17 (s, 12H). $^{13}$C NMR ($C_6D_6$, 125 MHz): δ 199.8, 199.3, 177.7, 135.5, 131.6, 129.3, 80.5, 65.8, 28.1, 19.0.

Dehydrogenative Coupling Conditions

With Ethylene (2 Atm or 8 Atm)

400 μL of 2 (5.0 mM) and p-xylene (3.0 mM) in toluene-$d_8$ solution was added to a medium-walled and sealable NMR tube, which was connected to a Kontes high-vacuum adapter with Tygon tubing. The Kontes valve was attached to a vacuum-gas manifold and the solution was frozen with liquid nitrogen. The headspace of the NMR tube was evacuated until the pressure reached 10 mTorr. The headspace was filled with 1 or 4 atm ethylene which was condensed by immersion in liquid nitrogen. After 30 sec, the NMR tube was sealed using an oxygen torch (the headspace volume was decreased by 50%, which brought the total ethylene pressure to 2 atm or 8 atm). The sealed NMR tube was allowed to reach room temperature, then heated while being rotated in a gas chromatography (GC) oven to promote gas-liquid mixing.

With Ethylene (12 Atm)

200 μL of 2 (5.0 mM) and p-xylene (3.0 mM) in toluene-$d_8$ solution was transferred to a heavy-walled NMR tube fitted with a re-sealable Teflon valve in a glovebox. The solution was degassed with a freeze-pump-thaw cycle and charged with 12 atm ethylene. The NMR tube was heated in an oil bath and shaken every 1 hour to promote gas-liquid mixing.

In the Presence of 1-Butene

200 μL of 2 (5.0 mM) and p-xylene (3.0 mM) in toluene-$d_8$ solution was transferred to a heavy-walled NMR tube fitted with a re-sealable Teflon valve in a glovebox. The solution was degassed with a freeze-pump-thaw cycle and charged with 2 psi of 1-butene. After shaking to promote gas-liquid mixing, the NMR tube was charged with 8 atm ethylene. The concentration of 1-butene in solution was determined to be 7.7 mM by $^1$H NMR spectroscopy. The NMR tube was heated in an oil bath and shaken every 1 hour to promote gas-liquid mixing.

In the Presence of 1,3-Butadiene

200 μL of 2 (5.0 mM) and p-xylene (3.0 mM) in toluene-$d_8$ solution and 20 μL of 1,3-butadiene (ca. 15 wt. %) in hexane solution was added to a heavy-walled NMR tube fitted with a re-sealable Teflon valve in a glovebox. The solution was degassed with a freeze-pump-thaw cycle and charged with 8 atm ethylene. The NMR tube was heated in an oil bath and shaken every 1 hour to promote gas-liquid mixing.

Ratio of 3 to 2 During Reaction

Following the procedure titled "With ethylene (2 atm or 8 atm)", reaction solutions with 2 atm, 4 atm, 6 atm and 8 atm ethylene were prepared, heated at 100° C. and monitored by $^1$H NMR spectroscopy every 25 min. The ratio of 3 to 2 was found to reach a steady state after 150 min. (Table 1)

TABLE 1

Ratio of 3 to 2 in the reaction under different pressure of ethylene.

| $PC_2H_4$ | 2 atm | 4 atm | 6 atm | 8 atm |
|---|---|---|---|---|
| [3]/[2] | 1.5 | 1.6 | 1.5 | 1.6 |

Gas Chromatographic Analysis Method

GC analyses (FID detection) were performed on a Varian 430-GC instrument fitted with Agilent J&W GS-GasPro column (60 m length, 0.32 mm ID) using the following method: Starting temperature: 40° C.; Time at starting temp: 1.4 min; Ramp1: 8° C./min up to 150° C. with hold time 3 min; Ramp2: 20° C./min up to 260° C. with hold time 30 min; Flow rate (carrier): 1.4 mL/min ($N_2$); Split ratio: 25; Injector temperature: 250° C.; Detector temperature: 260° C.

Computational Methods

All electronic structure calculations employed the DFT method. The M06-L exchange-correlation functional was used with the following choices of atomic basis sets: for Ir, the SDD relativistic effective (small) core potential and associated (6s5p3d) valence basis set, augmented with an f-type function and a complete set of diffuse spdf-type functions were applied (Andrae, et al. *Theor. Chim. Acta.*, 1990, 77, 123-141; Iron, et al. *J. Am. Chem. Soc.*, 2004, 126, 11699-11710); all-electron 6-311G(d,p) basis sets were applied to all other atoms (M06-L/SDD(+f+spdf)/6-311G(d,p)) (Ditchfield et al., *J. Chem. Phys.*, 1971, 54, 724-728; Hariharan, et al., *Molecular Physics*, 1974, 27, 209-214; Raghavachari, et al., *J. Chem. Phys.*, 1980, 72, 650-654). Reactant, transition state and product geometries were fully optimized using standard optimization procedures and characterized by normal mode analysis. For transition states (TSs) possessing an 'imaginary' frequency above ca. 100i cm$^{-1}$, the TS was connected to its representative reactant/product by carrying out Intrinsic Reaction Coordinate (IRC) calculations (Hratchian, et al., *J. Chem. Theory and Comput.* 2005, 1, 61-69). In some cases (small 'imaginary' frequencies), manually displacement of the TS structures in opposite directions along the transition vector (using GaussView8) was used, followed by geometry optimization toward a minimum to properly locate the matching reactant/product. Expanded integration grid sizes (pruned (99,590) atomic grids invoked in Gaussian 09 using the integral=ultrafine keyword) were applied to increase numerical accuracy and stability in geometry optimizations as well as normal mode analysis (Frisch, et al., Trucks Gaussian 09 User's Reference, 147). The (unscaled) vibrational frequencies formed the basis for the calculation of vibrational zero-point energy (ZPE) corrections. Standard thermodynamic corrections (based on the harmonic oscillator/rigid rotor approximations and ideal gas behavior) were made to convert from purely electronic potential energies (E) to (standard) enthalpies (H°, T=298.15 K) and Gibbs free energies (G°; T=298.15 K, P=1.0 atm). The polarizable conductor self-consistent reaction field model (CPCM; Barone, et al. *J. Phys. Chem. A*, 1998, 102, 1995-2001) was applied in all calculations to probe general bulk solvation effects. The solvent used experimentally in this study, p-xylene, was modeled using default parameters built into the chosen electronic structure code (Gaussian 09). All calculations were executed using the Gaussian 09 series of computer programs (Revision D.01).

Example 1: Catalytic Dehydrogenative Coupling of Ethylene Catalyzed by 2

Upon heating a toluene-$d_8$ solution of 2 (5.0 mM) under ethylene (2 atm) at 100° C. for 4 h, 1,3-butadiene (8.0 mM) and ethane (3.0 mM) were observed in solution by $^1$H NMR spectroscopy (eq 1). Surprisingly, only a minimal concentration of butenes (<1.0 mM) was observed in the $^1$H NMR spectrum, comprising only 8% of $C_4$ products (entry 1, Table 2) as determined by gas chromatography (GC).

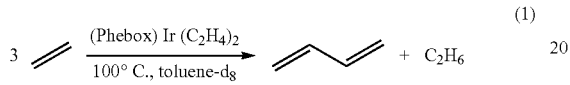

(1)

When an identical solution was heated for a longer time (16 h) the yield of butadiene was higher but the amount of butene as a percentage of $C_4$ products was significantly greater 21% (entry 2, Table 2). The latter observation suggests that the butadiene observed at the shorter reaction time was not a secondary product formed by the dehydrogenation of butene; it is instead consistent with the converse possibility that the butenes observed are formed as secondary products from butadiene hydrogenation.

Under higher pressures of ethylene (8 atm and 12 atm; entries 3 and 4, Table 2) greater yields of butadiene were obtained, with a relatively lower yield of butenes. When butadiene was added initially to the solution (entry 5), the net production of butadiene was much less, while the production of butene was significantly greater, consistent with the proposal that the butene is formed from butadiene. Accordingly, when the reaction is taken to higher conversion (with slightly longer times and a slightly higher temperature of 110° C.) significant yields of butene are obtained (entries 6-8). The formation of $C_6$ olefins is also observed at later times suggesting that these are also secondary products.

By removing the volatiles periodically (every 5.5 h) and replacing solvent and ethylene, greater total yields of butadiene and selectivity were achieved. After 21 h (4 cycles) a total of 101 mM butadiene had been produced, comprising 76% of the total olefins (entry 9, Table 2; FIG. 1).

TABLE 2

Dehydrogenative Ethylene Coupling Catalyzed by 2

| entry | temp/ ° C. | time | $P_{C_2H_4}$ | butadiene/mM (% total olefins) | butenes/ mM | $C_6$/ mM |
|---|---|---|---|---|---|---|
| 1 | 100 | 4 h | 2 atm | 8.0 (92%) | <1.0 | 0 |
| 2 | 100 | 16 h | 2 atm | 15 (68%) | 4.1 | 2.2 |
| 3 | 100 | 12 h | 8 atm | 23 (88%) | 2.1 | 1.3 |
| 4 | 100 | 12 h | 12 atm | 20 (90%) | 2.2 | 0 |
| 5 | 100[b] | 6 h | 8 atm | 6.1 (47%) | 6.2 | 0.7 |
| 6 | 110 | 18 h | 8 atm | 65 (62%) | 28 | 12 |
| 7 | 110 | 18 h | 12 atm | 70 (71%) | 20 | 8.2 |
| 8 | 110 | 21 h | 12 atm | 67 (62%) | 30 | 12 |
| 9 | 110[c] | 21 h | 12 atm | 101 (76%) | 21 | 11 |

[a]2 (5 mM) in toluene-$d_8$. To promote gas-liquid mixing the NMR tube was shaken periodically (entries 1-5, sealed NMR tube in an oven equipped with an internal rotator; entries 6-9, high-pressure J-Young tube manually shaken every 1 h).
[b]73 mM added butadiene.
[c]Volatiles removed every 5.5 h followed by recharging with toluene-$d_8$ and ethylene.

Example 2: Identification of Catalytic Intermediate Species

A toluene-$d_8$ solution of 2 was prepared with added 1-butene (7.7 mM). After 2 h at 100° C., under 8 atm ethylene, 8.8 mM butadiene had formed which was no different from an identical solution to which 1-butene had not been added. There was no change in the concentration of 1-butene, indicating that the butadiene was not formed from 1-butene. In addition, a similar experiment was conducted with added 1-butene (30 mM, isotopically unlabeled) under 2 atm ethylene-$d_4$. The resulting butadiene was completely butadiene-$d_6$, while the concentration of unlabeled 1-butene was unchanged, proving that the butadiene formation does not proceed via free 1-butene.

In the course of the catalytic runs (5 mM 2, ethylene, toluene-$d_8$, 100° C.), $^1$H NMR spectroscopy revealed the presence of a new species 3, along with 2. The ratio of 3 to 2 reached a steady state within ca. 4 h. It was found to be independent of ethylene pressure over a range from 2 atm-8 atm, with [3]/[2]=1.6±0.1.

The $^1$H NMR spectral data for 2 indicates $C_s$ symmetry, in contrast with the $C_{2v}$ symmetry of 2. A set of four multiplets is observed at δ1.53 (2H), δ 2.18 (2H), δ 2.55 (2H) and δ 3.74 ppm (2H). HCOSY NMR spectral data is consistent with the assignment of these peaks to a 1,4-butanediyl ligand. A broad singlet indicative of an ethylene ligand, is observed at δ 2.86 ppm (4H) with a corresponding signal at δ 53.19 ppm in the $^{13}$C NMR spectrum. Signals in the $^{13}$C NMR spectrum at δ 40.6, δ 36.4, δ 29.9 and δ 2.7 ppm are attributable to the butanediyl group. Based on this data, complex 3 is proposed to be an iridacyclopentane ethylene complex. Isolation of 3 from the mixture with 2 proved difficult, and attempts to grow X-ray-quality crystals directly from the mixture were unsuccessful.

Figure 2A:
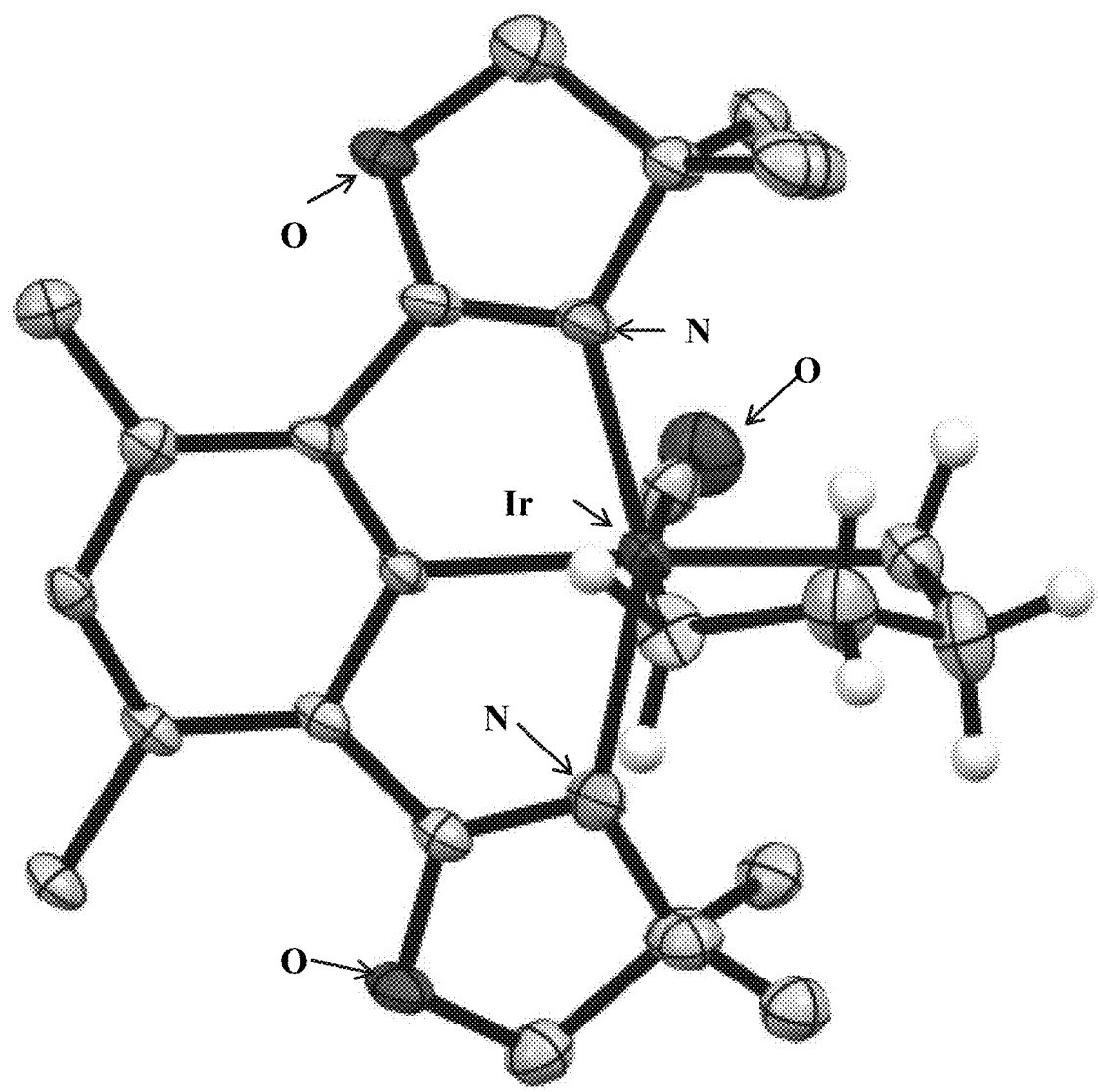
FIGS. 2A-2B are solid-state molecular structures of complex 6. Hydrogen atoms other than those of the iridacyclopentane ring were omitted for clarity in FIG. 2A. Gray unlabeled atoms are carbon atoms, and white unlabeled atoms are hydrogen atoms.

Addition of acetic acid (20 mM) to the $C_6D_6$ solution of 2 and 3 (3:7), immediately afforded a 3:7 mixture of (phebox)Ir(OAc)(ethyl) (1-ethyl) and (phebox)Ir(OAc)(n-butyl) (4) (eq 2). When an identical solution of 2 and 3 was exposed to 1 atm CO, the signals attributable to the ethylene ligands of both compounds quickly disappeared from the $^1$H NMR spectrum. The products were identified, on the basis of their $^1$H and $^{13}$C NMR spectra, as (Phebox)Ir(CO) (5) and 6, the product of substitution of the ethylene ligand of 2 by CO. X-ray-quality crystals of complex 6 from this mixture were obtained, which confirmed assignment of complex 6 (FIG. 2A), and by inference, assignment of 3.

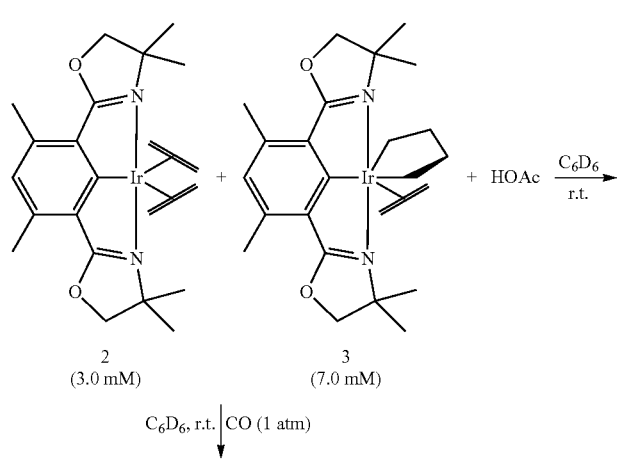
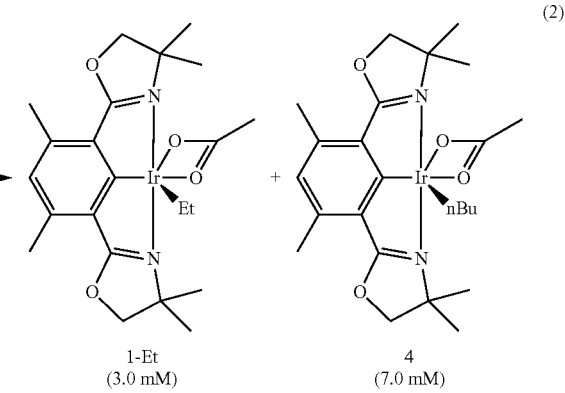

(2)

When a mixture of 2 (3.0 mM) and 3 (7.0 mM) in p-xylene-$d_{10}$ solution was heated under argon (1 atm) at 90° C., 2 was observed as the major species after 1 h. Further heating led to the decomposition of 2 with release of ethylene and the formation of only trace amounts (<0.5 mM) of $C_4$ hydrocarbons (eq 3).

(3)

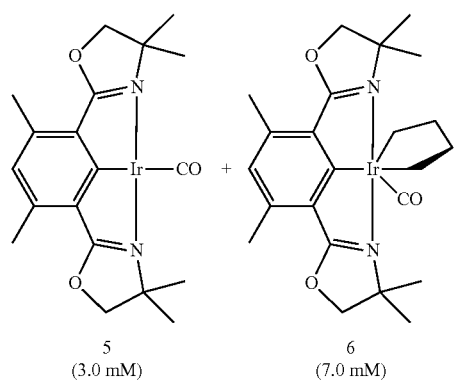

-continued

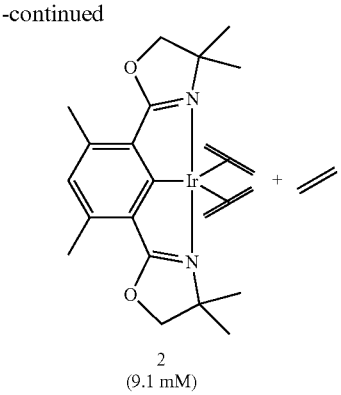

Example 3: X-Ray Structural Data for Complex 6

Single-crystal X-ray diffraction data were collected on a Bruker Smart APEX CCD diffractometer with graphite monochromatized Mo Kα radiation (λ=0.71073 Å) at 100 K. The crystals were immersed in oil and placed on a glass needle in the cold stream. The data were corrected for Lorenz effects, polarization, and absorption, the latter by a

Figure 2B:
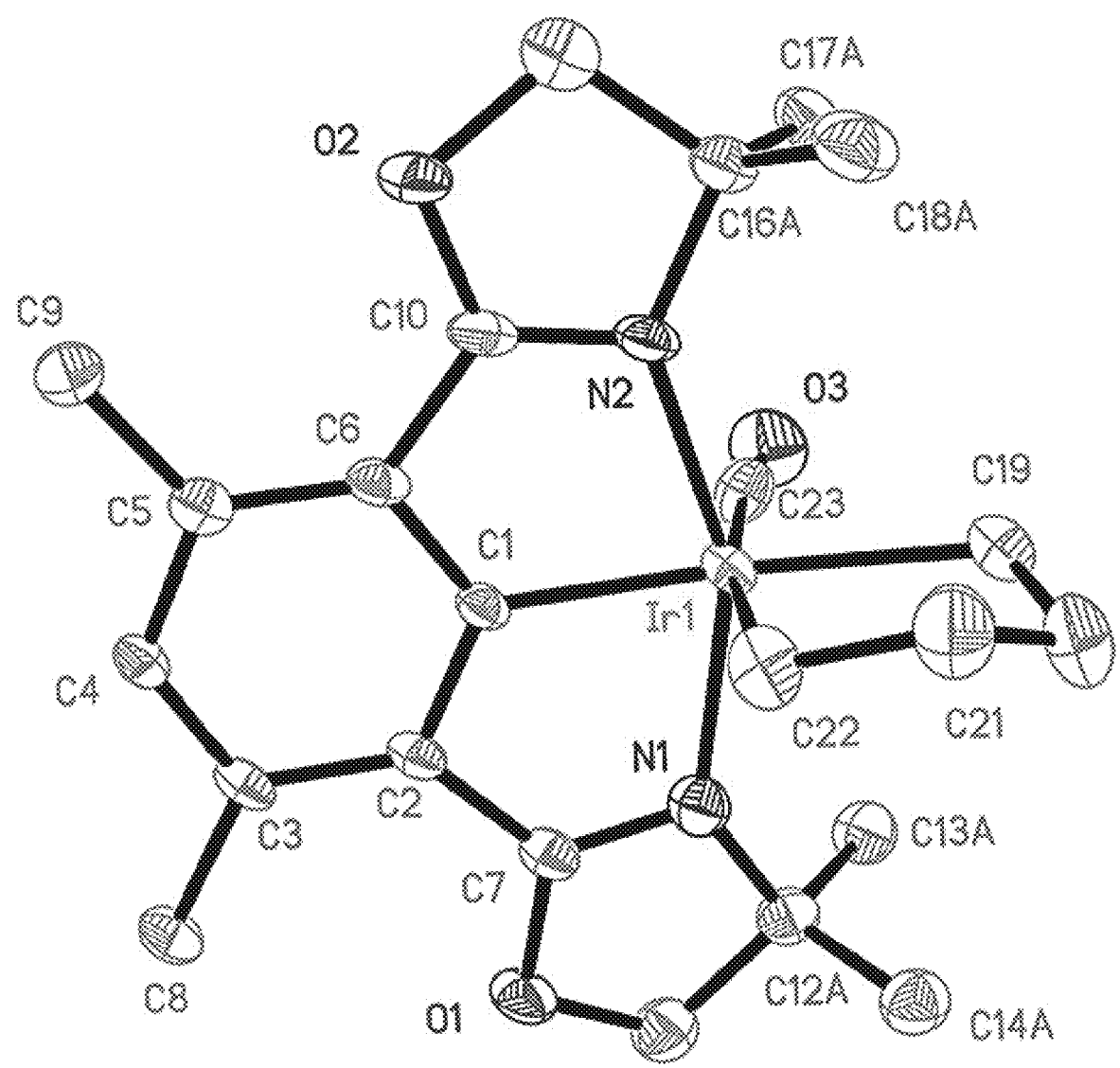

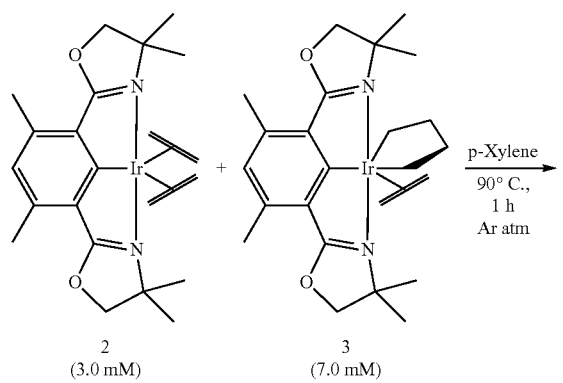

multi-scan method using program SAINT (Bruker (2013). APEX2, SAINT and SADABS. Bruker AXS Inc., Madison, Wis., USA). The structures were solved by direct methods using program SHELXS (Sheldrick, G. M. (2008). *Acta Cryst*. A64, 112-122.). Using program SHELXL (Sheldrick, G. M. (2015). *Acta Cryst*. C71, 3-8.) all non-hydrogen atoms were refined based upon Fobs and all hydrogen atom coordinates were calculated with idealized geometries. FIG. 2B depicts the ORTEP diagram of complex 6.

Example 4: Mechanistic Studies

A mixture of 2 and 3 was synthesized with $^{13}C_2H_4$, which resulted in full $^{13}$C-labeling of the 1,4-butanediyl unit of 3 and the ethylene ligands of both 2 and 3. The mixture of 2-$^{13}C_4$ (3.0 mM) and 3-$^{13}C_6$ (7.0 mM) in p-xylene-$d_{10}$ was then exposed to unlabeled ethylene (2 atm) at room temperature. The ethylene-$^{13}C_2$ ligands of both complexes were rapidly substituted by unlabeled ethylene ligand while free ethylene-$^{13}C_2$ was detected by $^1$H NMR and $^{13}$C NMR spectroscopy. No loss of $^{13}$C labeling of the 1,4-butanediyl group was observed, consistent with the higher temperatures required for interconversion of 2 and 3. Upon heating this mixture of unlabeled 1 and $^{13}C_4$-butanediyl labeled 3 at 100° C. for 30 min under an atmosphere of unlabeled $C_2H_4$, fully labeled ($^{13}C_4$) butadiene (1.7 mM) was observed in the $^1$H NMR spectrum, along with some unlabeled butadiene (0.6 mM). The formation of the $^{13}C_4$-labeled butadiene under an atmosphere of unlabeled $C_2H_4$, particularly as the major product, rules out the possibility that this butadiene formed via conversion of 3 to 2, as the latter undergoes rapid exchange with free ethylene.

Figure 3:
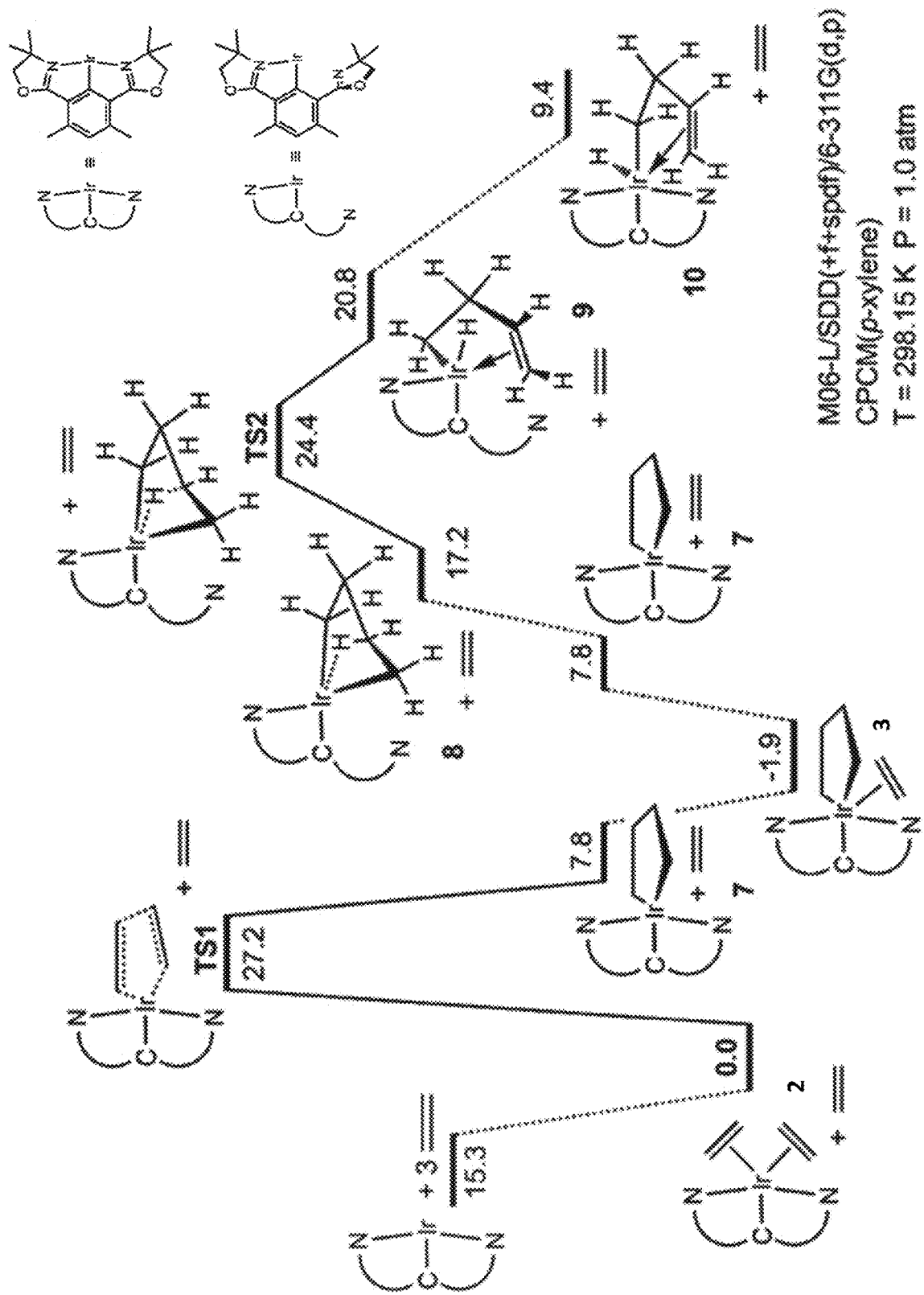
FIG. 3 is a free energy profile for ethylene coupling and β-H elimination of the resulting iridacyclopentane determined by DFT.

To determine the mechanism of eq 1, computational investigations (DFT) were undertaken, employing the M06-L functional, the SDD effective core potential on Ir, and valence basis sets of triple-zeta plus polarization quality (M06-L/SDD(+f+spdf)/6-311G(d,p)); some effects of solvation by p-xylene were included via a continuum dielectric model (CPCM/p-xylene). Complex 2 was calculated to undergo conversion to iridacyclopentane 3 via a concerted mechanism with activation parameters $\Delta H^{\ddagger}=26.7$ kcal/mol and $\Delta S^{\ddagger}=-1.7$ eu ($\Delta G^{\ddagger}=27.2$ kcal/mol at T=298 K, P=1 atm) to afford the 16-electron iridacyclopentane 7, followed by rapid coordination of ethylene to give 3 (FIG. 3). At 100° C. these activation parameters correspond to a rate of $7.6 \times 10^{-4}$ s$^{-1}$ or a half-life of ca. 900 s, in good agreement with the observation, noted above, that the reaction of 2 at 100° C. took several hours to reach a steady state ratio of 2 to 3.

Figure 4A:
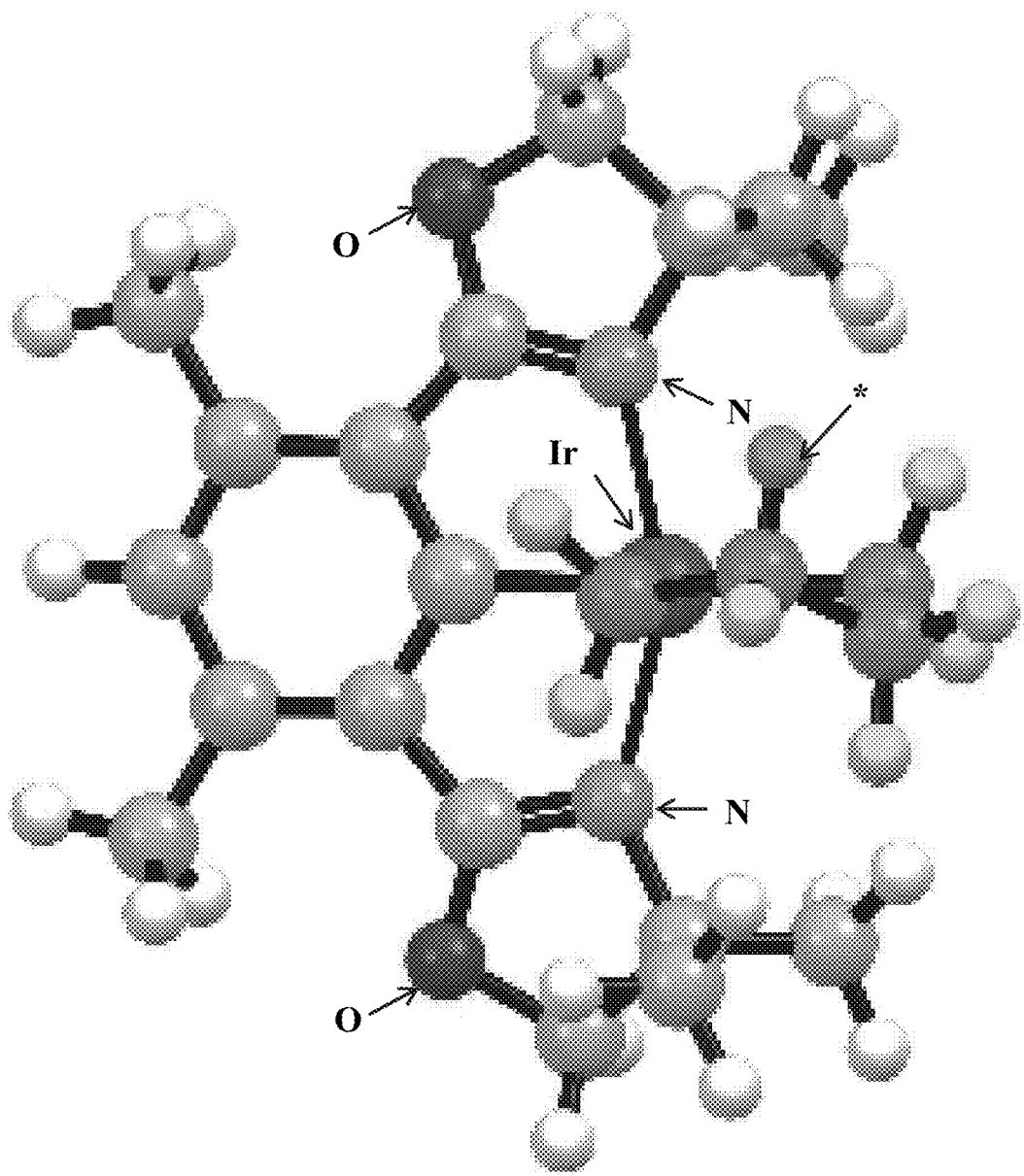
FIGS. 4A-4D are DFT structures of iridacyclopentane complex 7 (FIG. 4A), agostic iridacyclopentane complex 8
Figure 4B:
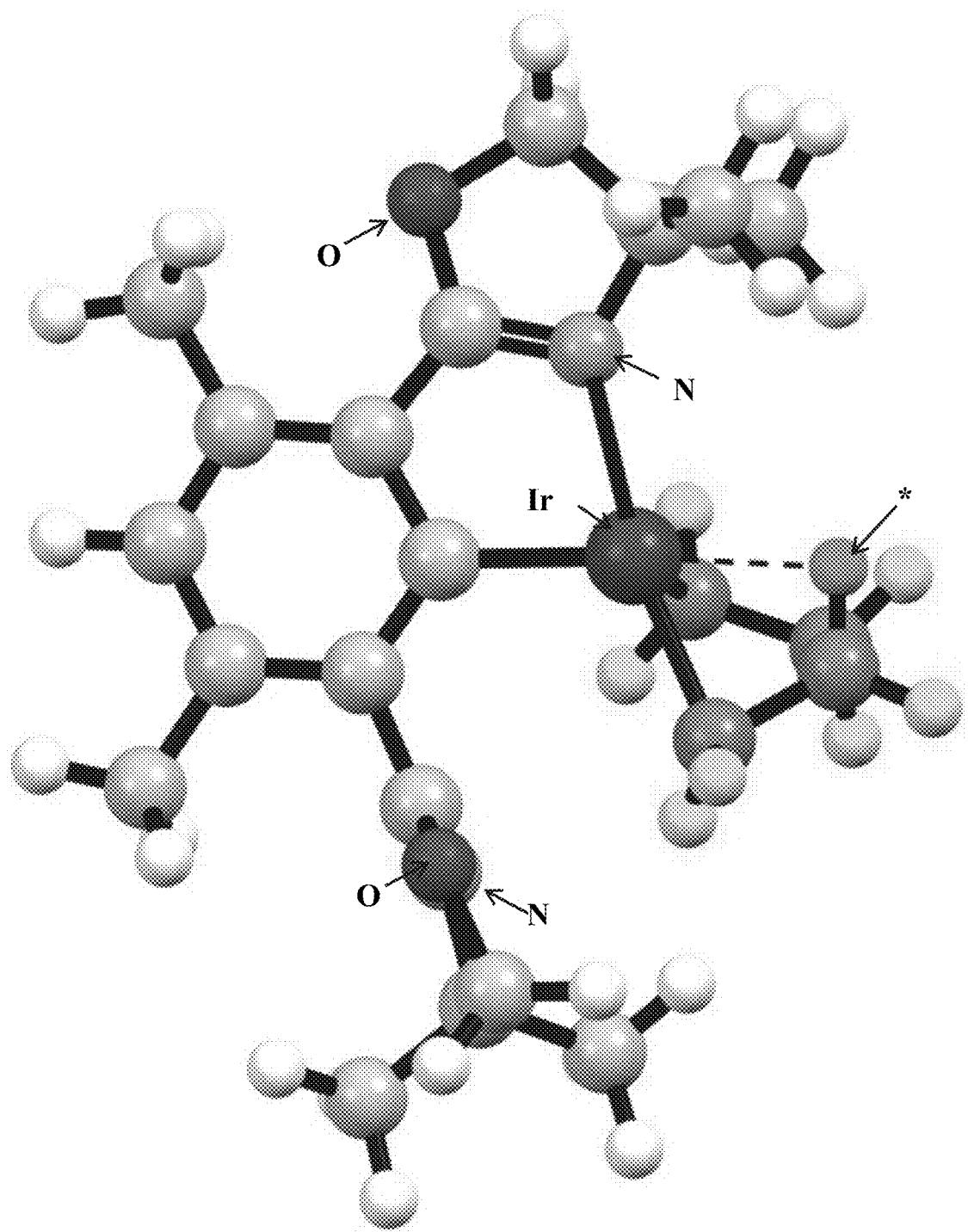
Figure 4C:
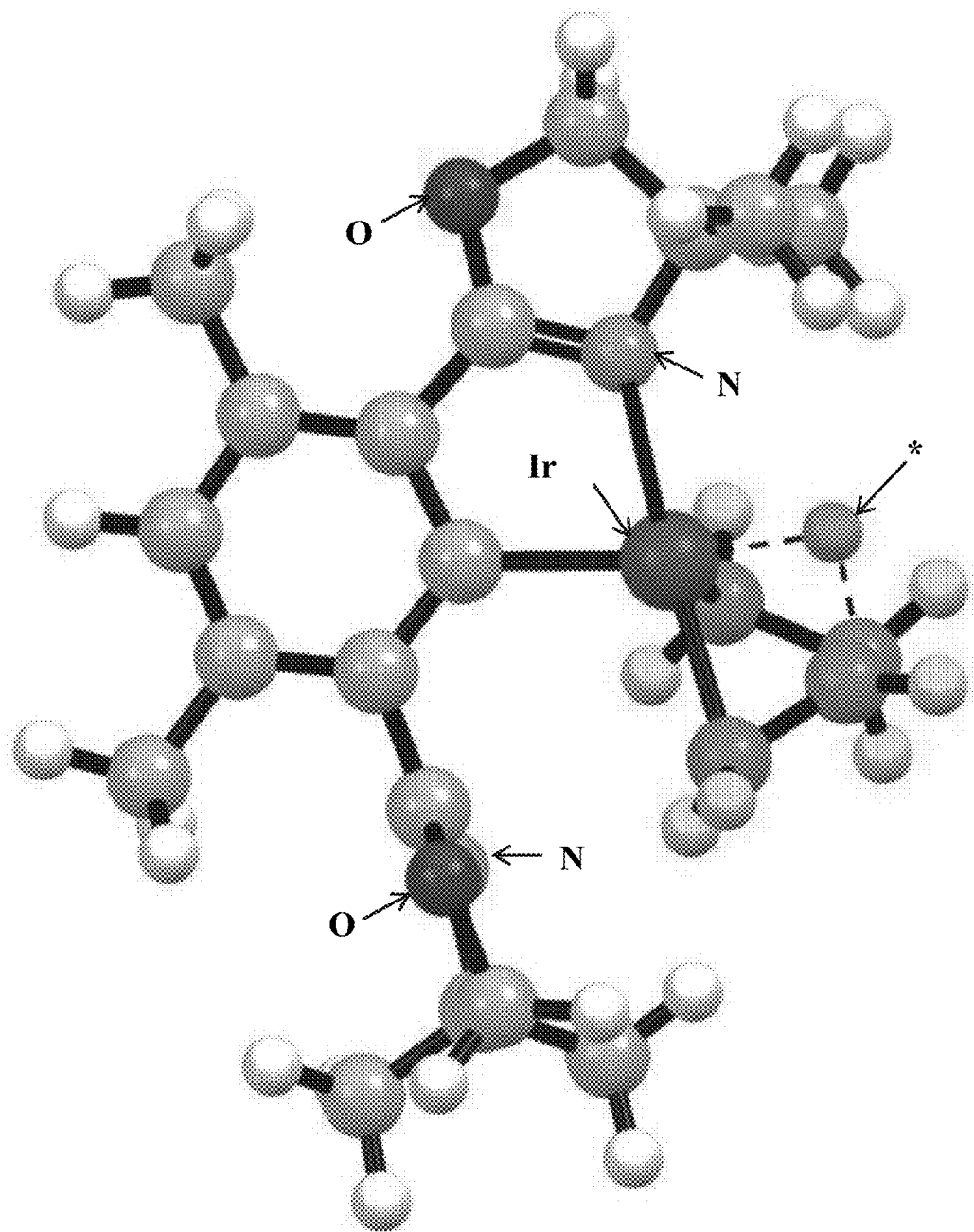

In the case of iridacyclopentane 3, DFT calculations revealed an unanticipated pathway for β-H-elimination. Loss of ethylene from 3 returns the 16-electron intermediate 7, which shows signs of steric crowding including a short H—H distance of 1.97 Å between the H atoms at C2 of the iridacyclopentane ring and the oxazoline methyl group. This is followed by the formation of an agostic interaction with a C(2)-H bond ($d_{Ir-H}=2.11$ Å), requiring the formation of a strongly puckered iridacyclopentane ring. Formation of this agostic complex (8, FIGS. 3 and 4B) would be sterically prohibitive but for an accompanying rotation around an oxazoline-aryl bond and thus loss of an N—Ir bond, i.e. $κ^3$-$κ^2$ partial dechelation of the Phebox ligand. The free energy of 8 is 17.2 kcal/mol above 2, or 9.4 kcal/mol above the non-agostic iridacyclopentane 7 (note that this energy includes the loss of an Ir—N bond).

Figure 4D:
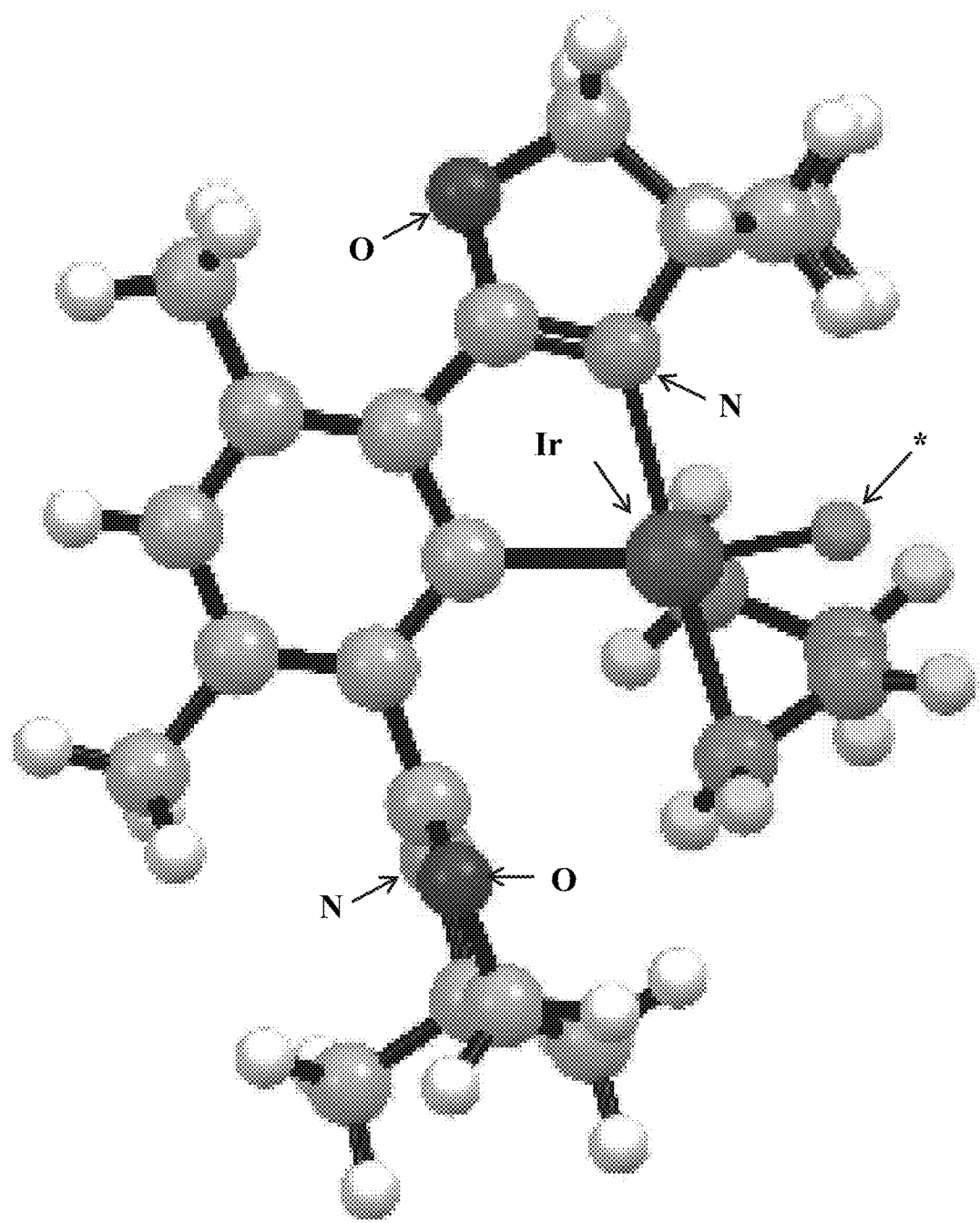

$\Delta G^{\ddagger}$ for β-H elimination from agostic complex 8 is 7.2 kcal/mol, corresponding to an overall barrier of 26.3 kcal/mol from 3. The β-H elimination leads to a 3-buten-1-yl hydride complex, 9, with the Phebox ligand still bound in a $κ^2$ configuration. Intermediate 9 may be described as approximately square pyramidal with C1 of the 3-buten-1-yl group in the apical position (FIG. 4D). The 3-buten-1-yl C═C double bond is approximately trans to the bound N (the N—Ir-centroid angle is 170°) while the hydride is approximately trans to the Ir-bound phebox aryl carbon atom (C—Ir—H=160°). Migration of the hydride to the vacant coordination site, accompanied by migration of the C═C double bond to the position formerly occupied by the hydride and coordination of the dangling oxazolinyl N atom would give the 18-electron $κ^3$-Phebox complex 10 with a free energy 1.6 kcal/mol above 7.

Figure 5:
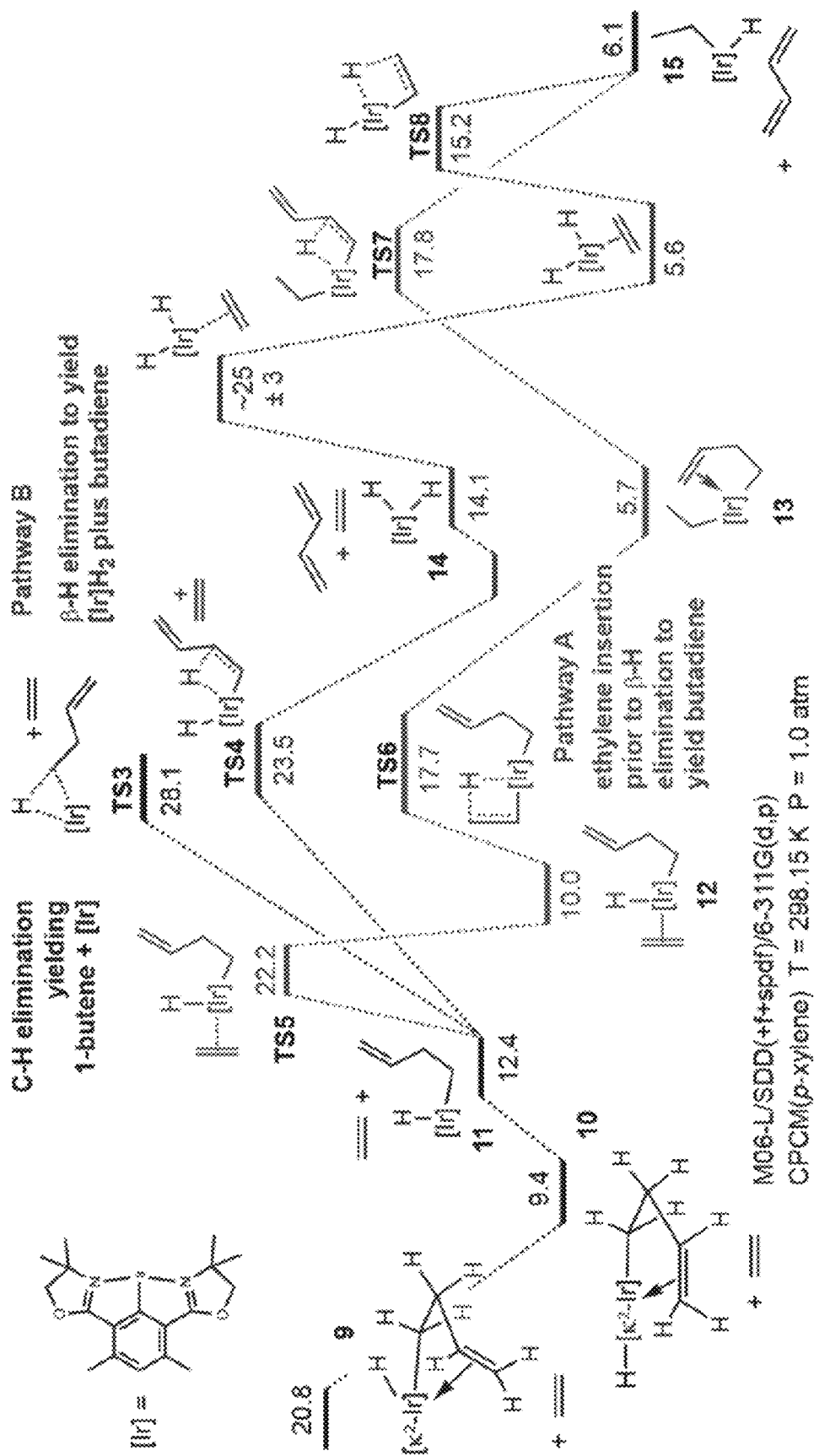
FIG. 5 is a free energy profile for butadiene formation following β-H elimination by iridacyclopentane 3.

Without intending to be limited to any particular theory, the apparent ease by which the Phebox ligand acts as a hemi-labile ligand, as indicated by the calculations, may be key to the surprisingly low barrier to β-H elimination of the metallacyclopentane. It is perhaps also important that the geometry of Phebox requires that upon dechelation the resulting "open" coordination site is not in fact very "open". The pendant oxazolinyl group necessarily remains close to the metal center, likely too close to allow coordination of another ligand (even one as small as ethylene), but not so close as to prevent puckering of the iridacyclopentane ring or slippage of the resulting butenyl vinyl group into the vacant coordination site.

β-H-elimination to give 9 may be followed by decoordination of the C—C double bond and re-coordination of the oxazoline N atom to give $κ^3$-Phebox complex 11 (possibly, but not necessarily, via $κ^3$-Phebox complex 10; FIG. 5). Complex 11 could then undergo C—H elimination to give 1-butene. The calculations predict, however, that the C—H elimination transition state TS3 is 4.6 kcal/mol higher in free energy than TS4 for β-H elimination (pathway shown in blue, FIG. 5). An even more favorable pathway, however, is calculated to proceed via insertion of ethylene into the Ir—H bond of 11 (following ethylene coordination to give 12). The free energies of TS4 and TS5 are probably not significantly different within the accuracy limits of the calculation, and the relative probability of 11 undergoing ethylene coordination and insertion ("TS5 pathway"), as opposed to β-H-elimination ("TS4 pathway"), may depend on ethylene concentration. Either through the TS4 or TS5 pathways, butadiene is formed via β-H-elimination of the 3-buten-1-yl group. By the TS4 pathway, (Phebox)IrH$_2$ (14) is produced, which is expected to undergo facile insertion of ethylene into an Ir—H bond. The two pathways thereby converge at (Phebox)IrH(Et) (15); elimination of ethane from 15 and coordination of two ethylene molecules then completes the catalytic cycle.

By proceeding via dihydride 14, the mechanism allows the possibility that 14 will hydrogenate the butadiene product to give 1-butene. This is consistent with the observation discussed above that higher pressures of ethylene lead to higher ratios of butadiene to 1-butene.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (Ia), or a salt or solvate thereof:

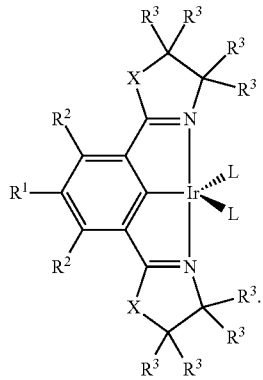

wherein:

X is O;

R$^1$ is selected from the group consisting of H, OH, halide, amine, C$_1$-C$_6$ alkyl, C$_3$-C$_8$ cycloalkyl, C$_1$-C$_8$ heteroalkyl, C$_3$-C$_8$ heterocycloalkyl, C$_1$-C$_6$ perhaloalkyl, C$_1$-C$_6$ alkoxy, aryl, heteroaryl, and benzyl;

each instance of R$^2$ is independently selected from the group consisting of H, OH, halide, amine, C$_1$-C$_6$ alkyl, C$_3$-C$_8$ cycloalkyl, C$_1$-C$_8$ heteroalkyl, C$_3$-C$_8$ heterocycloalkyl, C$_1$-C$_6$ perhaloalkyl, C$_1$-C$_6$ alkoxy, aryl, heteroaryl, and benzyl;

each instance of R$^3$ is independently selected from the group consisting of H, OH, halide, amine, C$_1$-C$_6$ alkyl, C$_3$-C$_8$ cycloalkyl, C$_1$-C$_8$ heteroalkyl, C$_3$-C$_8$ heterocycloalkyl, C$_1$-C$_6$ perhaloalkyl, and C$_1$-C$_6$ alkoxy;

each occurrence of L is independently selected from the group consisting of absent, CO, tetrahydrofuran, furan, pyran, tetrahydropyran, H$_2$O, benzene, toluene, cyclohexene, cyclooctene, cyclooctadiene, cyclopentene, pyridine, diethyl ether, acetonitrile, triphenyl phosphine, N-heterocyclic carbene, C$_1$-C$_6$ alcohol, pyrrole, pyrimidine, pyrrolidine, imidazole, and

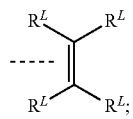

and each instance of R$^L$ is independently selected from the group consisting of H, C$_1$-C$_6$ alkyl, C$_3$-C$_8$ cycloalkyl, C$_2$-C$_8$ alkenyl, C$_2$-C$_8$ alkynyl, C$_1$-C$_8$ heteroalkyl, C$_3$-C$_8$ heterocycloalkyl, C$_2$-C$_8$ heteroalkenyl, C$_1$-C$_6$ perhaloalkyl, aryl, heteroaryl, and benzyl.

2. The compound of claim 1, wherein the compound of formula (Ia) is a compound of formula:

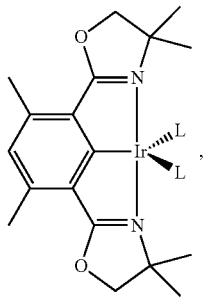

wherein L is

3. The compound of claim 1, wherein one instance of L is absent and the other instance of L is selected from the group consisting of absent, CO, tetrahydrofuran, furan, pyran, tetrahydropyran, H$_2$O, benzene, toluene, cyclohexene, cyclooctene, cyclooctadiene, cyclopentene, pyridine, diethyl ether, acetonitrile, triphenyl phosphine, N-heterocyclic carbene, C$_1$-C$_6$ alcohol, pyrrole, pyrimidine, pyrrolidine, imidazole, and

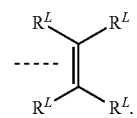

4. A compound of formula (II), or a salt or solvate thereof:

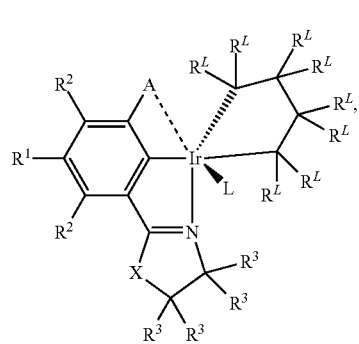

wherein:

A is

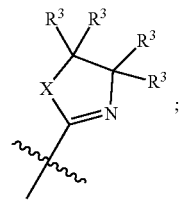

X is O;

R¹ is selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, $C_1$-$C_6$ alkoxy, aryl, heteroaryl, and benzyl;

each instance of R² is independently selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, $C_1$-$C_6$ alkoxy, aryl, heteroaryl, and benzyl;

each instance of R³ is independently selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, and $C_1$-$C_6$ alkoxy;

each occurrence of L is independently selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbene, $C_1$-$C_6$ alcohol, pyrrole, pyrimidine, pyrrolidine, imidazole, and

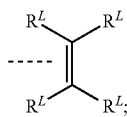

and each instance of $R^L$ is independently selected from the group consisting of H, $C_1$-$C_6$ alkyl, $C_3$-$C_8$ cycloalkyl, $C_2$-$C_8$ alkenyl, $C_2$-$C_8$ alkynyl, $C_1$-$C_8$ heteroalkyl, $C_3$-$C_8$ heterocycloalkyl, $C_2$-$C_8$ heteroalkenyl, $C_1$-$C_6$ perhaloalkyl, aryl, heteroaryl, and benzyl.

5. The compound of claim 4, wherein the compound of formula (II) is:

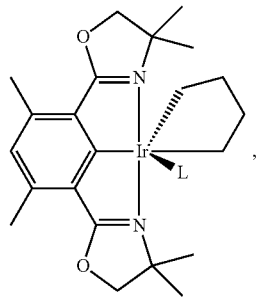

wherein L is

6. A method of catalytically converting an olefin comprising at least one vinylic hydrogen to a conjugated 1,3-diene, the method comprising contacting the olefin with a compound of formula (Ia), or a salt or solvate thereof:

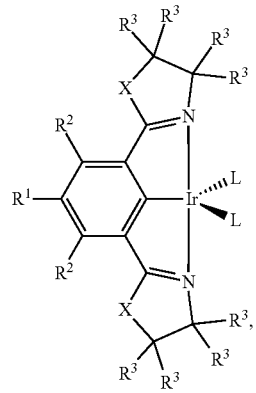

wherein:

X is O;

R¹ is selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, $C_1$-$C_6$ alkoxy, aryl, heteroaryl, and benzyl;

each instance of R² is independently selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, $C_1$-$C_6$ alkoxy, aryl, heteroaryl, and benzyl;

each instance of R³ is independently selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, and $C_1$-$C_6$ alkoxy;

each occurrence of L is independently selected from the group consisting of absent, CO, tetrahydrofuran, furan, pyran, tetrahydropyran, $H_2O$, benzene, toluene, cyclohexene, cyclooctene, cyclooctadiene, cyclopentene, pyridine, diethyl ether, acetonitrile, triphenyl phosphine, N-heterocyclic carbene, $Ci$-$C6$ alcohol, pyrrole, pyrimidine, pyrrolidine, imidazole, and

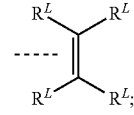

and each instance of $R^L$ is independently selected from the group consisting of H, $C_1$-$C_6$ alkyl, $C_3$-$C_8$ cycloalkyl, $C_2$-$C_8$ alkenyl, $C_2$-$C_8$ alkynyl, $C_1$-$C_8$ heteroalkyl, $C_3$-$C_8$ heterocycloalkyl, $C_2$-$C_8$ heteroalkenyl, $C_1$-$C_6$ perhaloalkyl, aryl, heteroaryl, and benzyl.

7. The method of claim 6, wherein the compound of formula (Ia) is a compound of formula (IV), and wherein the method comprises contacting a compound of formula (III) with a strong base (B) to generate a compound of formula (IV), and then contacting the compound of formula (IV) with the olefin:

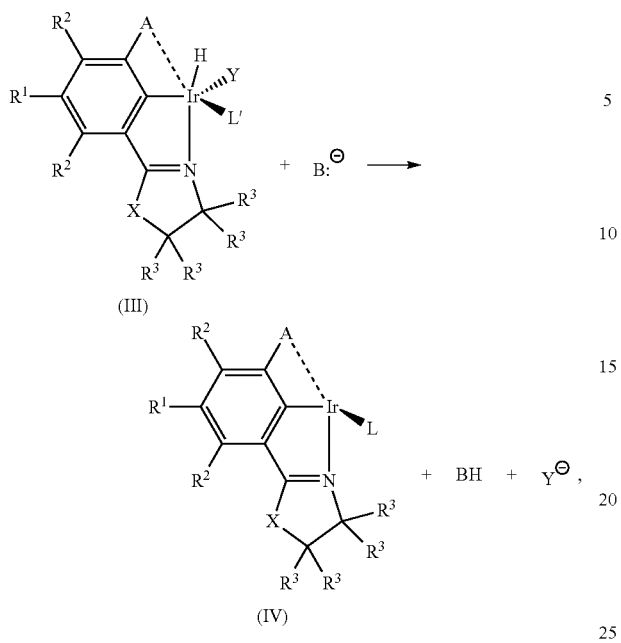

wherein
A is

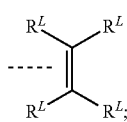

X is O;

R¹ is selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, $C_1$-$C_6$ alkoxy, aryl, heteroaryl, and benzyl;

each instance of R² is independently selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, $C_1$-$C_6$ alkoxy, aryl, heteroaryl, and benzyl;

each instance of R³ is independently selected from the group consisting of H, OH, halide, amine, $C_1$-$C_6$ alkyl, $C_3$-$C_8$ cycloalkyl, $C_1$-$C_8$ heteroalkyl, $C_3$-$C_8$ heterocycloalkyl, $C_1$-$C_6$ perhaloalkyl, and $C_1$-$C_6$ alkoxy;

each occurrence of L is independently selected from the group consisting of absent, CO, tetrahydrofuran, furan, pyran, tetrahydropyran, H₂O, benzene, toluene, cyclohexene, cyclooctene, cyclooctadiene, cyclopentene, pyridine, diethyl ether, acetonitrile, triphenyl phosphine, N-heterocyclic carbene, $C_1$-$C_6$ alcohol, pyrrole, pyrimidine, pyrrolidine, imidazole, and

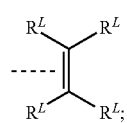

each instance of $R^L$ is independently selected from the group consisting of H, $C_1$-$C_6$ alkyl, $C_3$-$C_8$ cycloalkyl, $C_2$-$C_8$ alkenyl, $C_2$-$C_8$ alkynyl, $C_1$-$C_8$ heteroalkyl, $C_3$-$C_8$ heterocycloalkyl, $C_2$-$C_8$ heteroalkenyl, $C_1$-$C_6$ perhaloalkyl, aryl, heteroaryl, and benzyl; and either of the following applies:

i) Y is selected from the group consisting of $C_1$-$C_6$ carboxylate, $C_1$-$C_6$ amide, $OR^L$, halide, amide, thiolate, oxoanion, $C_1$-$C_6$ alkyl, $C_1$-$C_6$ alkyl, $C_3$-$C_8$ cycloalkyl, $C_2$-$C_8$ alkenyl, $C_2$-$C_8$ alkynyl, $C_1$-$C_8$ heteroalkyl, $C_3$-$C_8$ heterocycloalkyl, $C_2$-$C_8$ heteroalkenyl, $C_1$-$C_6$ perhaloalkyl, aryl, heteroaryl, and benzyl; and L' is selected from the group consisting of absent, CO, tetrahydrofuran, furan, pyran, tetrahydropyran, H₂O, benzene, toluene, cyclohexene, cyclooctene, cyclooctadiene, cyclopentene, pyridine, diethyl ether, acetonitrile, triphenyl phosphine, N-heterocyclic carbenes. $C_1$-$C_6$ alcohols, pyrrole, pyrimidine, pyrrolidine, imidazole, and

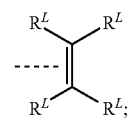

or ii) Y and L' are a single bidentate ligand selected from the group consisting of $C_1$-$C_6$ carboxylate and $C_1$-$C_6$ amide.

8. The method of claim 6, wherein the olefin is contacted at a pressure ranging from 0.1 atm to 100 atm.

9. The method of claim 6, wherein the compound is contacted with the alkene at a temperature of 100° C. to 200° C.

10. The method of claim 6, wherein the olefin comprises ethylene.

11. The method of claim 6, wherein the conjugated 1,3-diene comprises 1,3-butadiene.

12. The method of claim 6, wherein the compound is in solution.

13. The method of claim 12, wherein the solution comprises at least one solvent selected from the group consisting of toluene, benzene, xylenes, dioxane, heptane, pyridine, tetrahydrofuran, acetone, acetonitrile, butanol, butanone, carbon tetrachloride, chlorobenzene, chloroform, cyclohexane, dichloroethane, diethylene glycol, diethyl ether, diglyme, dimethyl formamide, dimethyl sulfoxide, ethanol, ethyl acetate, ethylene glycol, glycerin, hexamethylphosphoramide, hexamethylphosphorous triamide, hexanes, methanol, methylene chloride, N-methyl-2-pyrrolidinone, nitromethane, pentane, petroleum ether, propanol and triethylamine.

14. The method of claim 12, wherein the solution further comprises at least one hydrogen acceptor additive.

\* \* \* \* \*